(12) United States Patent
Bregman-Amitai et al.

(10) Patent No.: US 10,716,529 B2
(45) Date of Patent: Jul. 21, 2020

(54) SYSTEMS AND METHODS FOR PREDICTION OF OSTEOPOROTIC FRACTURE RISK

(71) Applicant: Zebra Medical Vision Ltd., Shefayim (IL)

(72) Inventors: Orna Bregman-Amitai, Tel-Aviv (IL); Eldad Elnekave, Tel-Aviv (IL)

(73) Assignee: Zebra Medical Vision Ltd., Shefayim (IL)

( * ) Notice: Subject to any disclaimer, the term of this patent is extended or adjusted under 35 U.S.C. 154(b) by 0 days.

(21) Appl. No.: 16/386,355

(22) Filed: Apr. 17, 2019

(65) Prior Publication Data

US 2019/0239843 A1    Aug. 8, 2019

Related U.S. Application Data

(63) Continuation of application No. 16/155,938, filed on Oct. 10, 2018, now Pat. No. 10,327,725, which is a
(Continued)

(51) Int. Cl.
*A61B 6/00*        (2006.01)
*A61B 6/03*        (2006.01)
*G06T 7/00*        (2017.01)

(52) U.S. Cl.
CPC ............ *A61B 6/5217* (2013.01); *A61B 6/032* (2013.01); *A61B 6/481* (2013.01); *A61B 6/482* (2013.01);
(Continued)

(58) Field of Classification Search
CPC ....... A61B 6/5217; A61B 6/032; A61B 6/481; A61B 6/482; A61B 6/505; A61B 6/5252; G06T 7/0012
See application file for complete search history.

(56) References Cited

U.S. PATENT DOCUMENTS 8,818,484 B2    8/2014    Liew et al.
8,831,305 B2    9/2014    Zhang et al.
(Continued)

FOREIGN PATENT DOCUMENTS

WO    WO 2016/013004    1/2016
WO    WO 2016/013005    1/2016

OTHER PUBLICATIONS

Notice of Allowance dated Jan. 17, 2020 From the US Patent and Trademark Office Re. U.S. Appl. No. 16/346,123. (16 pages).
(Continued)

*Primary Examiner* — Mia M Thomas

(57) ABSTRACT

There is provided a method for predicting risk of osteoporotic fracture, comprising: receiving imaging data of a computed tomography (CT) scan of a body of a patient containing at least a bone portion, the CT scan being performed with settings selected for imaging of non-osteoporosis related pathology; processing the imaging data to identify the bone portion; automatically extracting features based on the imaging data denoting the identified bone portion; computing an osteoporotic fracture predictive factor indicative of the risk of developing at least one osteoporotic fracture in the patient, or the risk of the patient having at least one severe osteoporotic fracture, based on the extracted features, the predictive factor calculated by applying a trained osteoporotic fracture classifier to the extracted features, the osteoporotic fracture classifier trained from data from a plurality of CT scans performed with settings selected for imaging non-osteoporosis related pathology; and providing the predictive factor.

20 Claims, 6 Drawing Sheets

Related U.S. Application Data continuation of application No. 15/964,086, filed on Apr. 27, 2018, now Pat. No. 10,111,637, which is a continuation of application No. 14/726,813, filed on Jun. 1, 2015, now Pat. No. 10,039,513.

(60) Provisional application No. 62/026,730, filed on Jul. 21, 2014.

(52) U.S. Cl.
CPC ............ *A61B 6/505* (2013.01); *A61B 6/5252* (2013.01); *G06T 7/0012* (2013.01); *G06T 2207/10081* (2013.01); *G06T 2207/20081* (2013.01); *G06T 2207/30012* (2013.01)

(56) References Cited

U.S. PATENT DOCUMENTS

| | | | |
|---|---|---|---|
| 8,855,389 B1 | 10/2014 | Hoffmann et al. | |
| 8,913,818 B2* | 12/2014 | Lang ...................... | A61B 6/505 382/132 |
| 8,923,594 B2 | 12/2014 | Wehnes et al. | |
| 8,965,075 B2 | 2/2015 | Arnaud et al. | |
| 9,153,021 B2 | 10/2015 | Wilson | |
| 9,155,501 B2 | 10/2015 | Lang et al. | |
| 9,211,103 B2 | 12/2015 | Kraus et al. | |
| 9,267,955 B2 | 2/2016 | Lang et al. | |
| 9,274,037 B2 | 3/2016 | Huwer et al. | |
| 9,532,750 B2 | 1/2017 | Dzyubak et al. | |
| 9,589,204 B2 | 3/2017 | Gremse et al. | |
| 9,775,577 B2 | 10/2017 | Chang et al. | |
| 9,848,818 B1 | 12/2017 | Kopperdahl et al. | |
| 9,936,934 B2 | 4/2018 | Kopperdahl et al. | |
| 9,940,711 B2 | 4/2018 | Bregman-Amitai et al. | |
| 10,039,513 B2 | 8/2018 | Bregman-Amitai et al. | |
| 10,111,637 B2 | 10/2018 | Bregman-Amitai et al. | |
| 10,492,719 B2* | 12/2019 | Kopperdahl ........... | G16H 15/00 |
| 10,600,185 B2* | 3/2020 | Yang ....................... | G06T 7/187 |
| 2002/0009215 A1 | 1/2002 | Armato, III et al. | |
| 2002/0075997 A1 | 6/2002 | Unger et al. | |
| 2002/0181651 A1 | 12/2002 | Shepherd et al. | |
| 2002/0191823 A1 | 12/2002 | Wehrli et al. | |
| 2003/0179915 A1* | 9/2003 | Goto ....................... | G06T 7/0012 382/128 |
| 2004/0101104 A1 | 5/2004 | Avinash et al. | |
| 2004/0120922 A1 | 6/2004 | Burke | |
| 2004/0171931 A1 | 9/2004 | Barth et al. | |
| 2006/0062442 A1 | 3/2006 | Arnaud et al. | |
| 2006/0106459 A1 | 5/2006 | Truckai et al. | |
| 2007/0223799 A1 | 9/2007 | Weiss | |
| 2008/0008366 A1* | 1/2008 | Desh ....................... | G06T 19/00 382/128 |
| 2008/0025584 A1 | 1/2008 | Kunz et al. | |
| 2008/0082002 A1 | 4/2008 | Wilson et al. | |
| 2008/0216845 A1 | 9/2008 | De Bruijne et al. | |
| 2008/0310717 A1* | 12/2008 | Saathoff ................ | G06T 7/187 382/173 |
| 2009/0093852 A1 | 4/2009 | Hynes | |
| 2009/0185731 A1* | 7/2009 | Ray .......................... | G06T 7/149 382/131 |
| 2009/0226060 A1* | 9/2009 | Gering ...................... | G06T 7/143 382/128 |
| 2009/0297012 A1 | 12/2009 | Brett et al. | |
| 2010/0030064 A1* | 2/2010 | Averbuch ................ | G06T 7/337 600/424 |
| 2010/0111395 A1 | 5/2010 | Tamakoshi | |
| 2010/0177946 A1 | 7/2010 | De Bruijne et al. | |
| 2010/0310141 A1 | 12/2010 | Wilson | |
| 2011/0036360 A1 | 2/2011 | Lang et al. | |
| 2011/0142307 A1 | 6/2011 | Ghosh et al. | |
| 2011/0158494 A1 | 6/2011 | Bar-Shalev et al. | |
| 2011/0208033 A1 | 8/2011 | Nicolella et al. | |
| 2011/0257507 A1 | 10/2011 | Gregory et al. | |
| 2011/0317898 A1 | 12/2011 | Shi et al. | |
| 2012/0004594 A1 | 1/2012 | Schulz et al. | |
| 2012/0143090 A1 | 6/2012 | Hay et al. | |
| 2013/0004043 A1 | 1/2013 | Ross et al. | |
| 2013/0077840 A1 | 3/2013 | Blumfield et al. | |
| 2013/0137988 A1 | 5/2013 | Bregman-Amitai et al. | |
| 2013/0150700 A1 | 6/2013 | Kalvesten et al. | |
| 2013/0259190 A1 | 10/2013 | Walls et al. | |
| 2013/0301794 A1 | 11/2013 | Grader et al. | |
| 2014/0072571 A1 | 3/2014 | Urdea et al. | |
| 2014/0177788 A1 | 6/2014 | Stevens et al. | |
| 2014/0275705 A1 | 9/2014 | Virshup et al. | |
| 2014/0336503 A1 | 11/2014 | Kilbourn et al. | |
| 2014/0371570 A1 | 12/2014 | Davis et al. | |
| 2015/0110373 A1 | 4/2015 | Shaham et al. | |
| 2015/0164454 A1 | 6/2015 | Grant et al. | |
| 2015/0173703 A1 | 6/2015 | Siewerdsen et al. | |
| 2015/0196264 A1 | 7/2015 | Luo et al. | |
| 2015/0348259 A1 | 12/2015 | Souza et al. | |
| 2016/0015347 A1 | 1/2016 | Bregman-Amitai et al. | |
| 2016/0045733 A1 | 2/2016 | McGeoch et al. | |
| 2016/0113612 A1 | 4/2016 | Sedlmair et al. | |
| 2016/0151026 A1 | 6/2016 | Shibasaki et al. | |
| 2016/0183355 A1 | 6/2016 | Lou et al. | |
| 2016/0302748 A1 | 10/2016 | Chang et al. | |
| 2016/0328631 A1* | 11/2016 | Lay ......................... | G06T 7/162 |
| 2016/0338649 A1 | 11/2016 | Branch et al. | |
| 2017/0148156 A1* | 5/2017 | Bregman-Amitai ... | A61B 6/481 |
| 2018/0075628 A1 | 3/2018 | Teare | |
| 2018/0116584 A1* | 5/2018 | Kopperdahl ........... | A61B 6/463 |
| 2018/0242943 A1* | 8/2018 | Bregman-Amitai ... | A61B 6/505 |
| 2018/0259608 A1 | 9/2018 | Golden et al. | |
| 2018/0333140 A1 | 11/2018 | Wodlinger et al. | |
| 2019/0046146 A1 | 2/2019 | Bregman-Amitai et al. | |
| 2019/0336097 A1* | 11/2019 | Bregman-Amitai ... | G06K 9/627 |
| 2019/0340752 A1 | 11/2019 | Brestel et al. | |
| 2019/0340753 A1* | 11/2019 | Brestel .................. | G06T 7/0012 |
| 2019/0340763 A1 | 11/2019 | Laserson | |

OTHER PUBLICATIONS

International Preliminary Report on Patentability dated Feb. 2, 2017 From the International Bureau of WIPO Re. Application No. PCT/IL2015/050743. (6 Pages).
International Preliminary Report on Patentability dated Feb. 2, 2017 From the International Bureau of WIPO Re. Application No. PCT/IL2015/050744. (9 Pages).
International Search Report and the Written Opinion dated May 17, 2016 From the International Searching Authority Re. Application No. PCT/IL2015/050744.
International Search Report and the Written Opinion dated Dec. 22, 2015 From the International Searching Authority Re. Application No. PCT/IL2015/050743.
Invitation to Pay Additional Fees dated Dec. 4, 2015 From the International Searching Authority Re. Application No. PCT/IL2015/050744.
Official Action dated Jun. 2, 2017 from the US Patent and Trademark Office Re. U.S. Appl. No. 14/726,813. (36 pages).
AOSpine "Spinal Fractures Classification System" AOSpine Knowledge Forum, 2016, 72 pages.
Carberry et al. "Unreported Vertebral Body Compression Fractures at Abdominal Multidetector CT", Radiology, 268(1): 120-126, Jul. 2013.
Cummings et al. "Epidemiology and Outcomes of Osteoporotic Fractures", The Lancet, 359: 1761-1767, May 18, 2002.
Davidson et al. "Protocol for Measurement of Liver Fat by Computed Tomography," Journal of Applied Physiology 100: 864-868, 2006.
Engelke et al. "Clinical Use of Quantitative Computed Tomography and Peripheral Quantitative Computed Tomography in the Management of Osteoporosis in Adults: The 2007 ISCD Official Positions", Journal of Clinical Densitometry: Assessment of Skeletal Health, 11(1): 123-162, Jan.-Mar. 2008.
Harrigan et al. "Predicting Bone Mechanical Properties of Cancellous Bone from DXA, MRI, and Fractal Dimensional Measurements." Final Report, TMC-NASA Collaborative Research Project, 1997, 6 pages.

(56) References Cited

OTHER PUBLICATIONS

Kanis "Diagnosis of Osteoporosis and Assessment of Fracture Risk", The Lancet, 359: 1929-1936, Jun. 1, 2002.

Kanis et al. "European Guidance for the Diagnosis and Management of Osteoporosis in Postmenopausal Woman", Osteoporosis International, 24: 23-57, 2013.

Keenan et al. "Comparison of Bone Density Measurement Techniques: DXA and Archimedes' Principle." Journal of Bone and Mineral Research 12(11): 1903-1907, 1997.

Langer "A Flexible Database Architecture for Mining DICOM Objects: The DICOM Data Warehouse", Journal of Digital Imaging, 25: 206-212, 2012.

Link "Osteoporosis Imaging: State of the Art and Advanced Imaging", Radiology, 263(1): 3-17, Apr. 2012.

Majumdar et al. "Conventional Computed Tomography Imaging and Bone Mineral Density: Opportunistic Screening or 'Incidentaloposis'?", Annals of Internal Medicine, 158: 630-631, 2013.

Nguyen et al. "Osteoporosis: Underrated, Underdiagnosed and Undertreated", The Medical Journal of Australia, MJA, 1805/Suppl.): S18-S22, Mar. 1, 2004.

Pickhardt et al. "Opportunistic Screening for Osteoporosis Using Abdominal Computed Tomography Scans Obtained for Othe Indications", Annals of Internal Medicine, 158: 588-595, 2013.

Pickhardt et al. "Simultaneous Screening for Osteoporosis at CT Colonography: Bone Mineral Density Assessment Using MDCT Attenuation Techniques Compared Against the DXA Reference Standard", Journal of Bone and Mineral Research, 26(9): 2194-2203, Sep. 2011.

Rajasekaran et al. "The Value of CT and MRI in the Classification and Surgical Decision-Making Among Spine Surgeons in Thoracolumbar Spinal Injuries." European Spine Journal (Jun. 1, 2016): 1-7.

Reinhold et al. "AO Spine Injury Classification System: a Revision Proposal for the Thoracic and Lumbar Spine." European Spine Journal 22(10): 2184-2201, 2013.

Schwaiger et al. "Bone Mineral Density Values Derived From Routine Lumbar Spine Multidetector Row CT Predict Osteoporotic Vertebral Fractures and Screw Loosening", American Journal of Neuroradiology, AJNR, p. 1-6, Mar. 13, 2014.

Siris et al. "Identification and Fracture Outcomes of Undiagnosed Low Bone Mineral Density in Postmenopausal Women", Journal of the American Medical Association, JAMA, 286(22): 2815-2822, Dec. 12, 2001.

Summers et al. "Feasibility of Simultaneous CT Colonography and Fully-Automated Bone Mineral Densitometry in a Single Examination", Journal of Computer Assisted Tomography, 35(2): 212-216, Mar.-Apr. 2011.

Wahner "The Evaluation of Osteoporosis: Dual Energy X-ray Absorptiometry in Clinical Practice," Book Review, European Journal of Radiology 19: 151-153, 1995.

Williams et al. "Under-Reporting of Osteoporotic Vertebral Fractures on Computed Tomography", European Journal of Radiology, 69: 179-183, 2009.

\* cited by examiner

SYSTEMS AND METHODS FOR PREDICTION OF OSTEOPOROTIC FRACTURE RISK

RELATED APPLICATIONS

This application is a continuation of U.S. patent application Ser. No. 16/155,938 filed on Oct. 10, 2018, which is a continuation of U.S. patent application Ser. No. 15/964,086 filed on Apr. 27, 2018, now U.S. Pat. No. 10,111,637, which is a continuation of U.S. patent application Ser. No. 14/726,813 filed on Jun. 1, 2015, now U.S. Pat. No. 10,039,513, which claims the benefit of priority under 35 USC § 119(e) of U.S. Provisional Patent Application No. 62/026,730 filed on Jul. 21, 2014.

The contents of the above applications are all incorporated by reference as if fully set forth herein in their entirety.

BACKGROUND OF THE INVENTION

The present invention, in some embodiments thereof, relates to systems and methods for detection of osteoporotic fractures and, more specifically, but not exclusively, to systems and methods for automatic prediction of osteoporotic fractures based on medical imaging data and optionally with information from the patient electronic health record (EHR).

Osteoporosis remains a prevalent, burdensome and markedly under-diagnosed condition. DXA (Duel-Energy X-ray Absorptiometry) remains the diagnostic standard for assessing bone mineral density (BMD). However, fewer than 50% of eligible Medicare recipients undergo bone mineral density screening. Underutilization of DXA together with suboptimal test predictive indices may account for the finding that an estimated 80% of patients who experience osteoporotic fractures have either not undergone prior screening or received appropriate treatment. It is important to note that early diagnosis and prophylactic treatment can reduce the risk of osteoporotic fractures by 30-70%.

SUMMARY OF THE INVENTION

According to an aspect of some embodiments of the present invention there is provided a computer-implemented method for predicting risk of osteoporotic fracture, comprising: receiving imaging data of a computed tomography (CT) scan of a body of a patient containing at least a bone portion, the CT scan being performed with settings selected for imaging of non-osteoporosis related pathology; processing the imaging data to identify the bone portion; automatically extracting features based on the imaging data denoting the identified bone portion; computing an osteoporotic fracture predictive factor indicative of the risk of developing at least one osteoporotic fracture in the patient, or the risk of the patient having at least one severe osteoporotic fracture, based on the extracted features, the osteoporotic fracture predictive factor calculated by applying a trained osteoporotic fracture classifier to the extracted features, the osteoporotic fracture classifier trained from data from multiple CT scans performed with settings selected for imaging non-osteoporosis related pathology; and providing a signal indicative of the osteoporotic fracture predictive factor.

Optionally, the imaging data includes age and gender of the patient.

Optionally, the method further comprises computing a current bone state rating for the patient based on the extracted features.

Optionally, the method further comprises computing an estimate of the probability of the patient being in a certain bone grade state within a predefined time period based on the trained osteoporotic fracture classifier applied to the extracted features.

Optionally, the osteoporotic fracture predictive factor is calculated when less than all of the extractable features are successfully extracted.

Optionally, the method further comprises normalizing the received CT scan based on at least one imaging parameter such that extracted features from different CT scans are standardized for comparison to one another.

Optionally, the method further comprises assigning a validity score to each of the extracted features denoting estimated success or failure of the respective extracted feature based on the ability to correctly extract the respective feature from the imaging data, and excluding extracted features having validity scores below a threshold.

Optionally, the method further comprises assigning a validity score to each of the extracted features denoting estimated success or failure of the respective extracted feature based on the ability to correctly extract the respective feature from the imaging data, and providing confidence for the calculated risk as function of the validity of the extracted features.

Optionally, the classifier is trained based on training imaging files from at least some patients diagnosed with osteoporosis that have undergone multiple CT scans for non-osteoporosis related pathology at different periods in time that are long enough to detect statistically significant changes in at least some of the extracted features.

Optionally, the classifier is trained based on training imaging files from at least some patients that have undergone multiple CT scans for non-osteoporosis related pathology at different periods in time that are long enough to detect statistically significant changes in at least some of the extracted features, and wherein one or more osteoporosis fractures were detected in the latest scan and were not detected in the earlier scan.

Optionally, the classifier is trained based on training imaging files from a group of patient having pre-selected demographic characteristics.

Optionally, the classifier is trained based on training imaging files from a group of patient with common pathology.

Optionally, the classifier is trained based on training imaging files from a group of patient under similar medical treatments.

Optionally, the osteoporotic fracture predictive factor includes a time frame for a risk of developing or having at least one osteoporotic fracture.

Optionally, the osteoporotic fracture predictive factor includes an adjusted risk of developing or having at least one osteoporotic fracture based on at least one demographic parameter.

Optionally, the osteoporotic fracture predictive factor includes an adjusted risk of developing or having at least one osteoporotic fracture based on at least one pathological parameter.

Optionally, the CT scan data is inadequate for estimating a bone mineral density (BMD) measurement of the bone portion.

Optionally, the CT scan data is inadequate for performing a quantitative computed tomography scan (QCT) for measurement of BMD.

Optionally, the received CT scan and the multiple CT scans for training the classifier have been ordered for diagnosis of non-osteoporosis medical conditions based on non-osteoporosis related signs and/or symptoms.

Optionally, the trained osteoporotic fracture classifier is based on multiple weak classifiers, each weak classifier being unable to calculate the osteoporotic fracture predictive factor with a statistical certainty above a random guess, the multiple weak classifier being boosted to generate the trained osteoporotic fracture classifier that calculates the osteoporotic fracture factors with a statistical certainty above a random guess.

Optionally, the osteoporotic fracture predictive factor is indicative of the risk of developing an osteoporotic vertebral body fracture or hip fracture.

Optionally, automatically extracting features comprises automatically extracting features from at least a portion of at least one identified segmented vertebrae bone. Optionally, the extracted features denote a calculated Hounsfield index based on volumetric information of at least one identified segmented vertebrae. Alternatively or additionally, the extracted feature denotes a trabecular texture characteristic of the vertebral trabecular bone structure associated with degradation of the micro-architecture of bone tissue. Alternatively or additionally, the extracted feature denotes one or both of vertebra cortical width and vertebral cortical regularity.

Optionally, automatically extracting features comprises automatically extracting features associated with a risk of osteoporotic fractures. Optionally, the extracted features are associated with the risk of osteoporotic fractures include at least one member of a group consisting of: vertebra upper edge flatness, vertebra upper and lower edge angles, vertebrae height changes, and spinal column similarity to healthy model. Optionally, the automatically extracted features associated with osteoporotic fractures are based on an analysis of the structure of the spine based on identified vertebrae and relation between vertebrae sizes.

Optionally, the method further comprises automatically extracting medical history parameters from a medical history of the patient, and computing the osteoporotic fracture predictive factor based on the extracted medical history parameters.

Optionally, identifying comprises automatically segmenting at least one spinal bone portion from the CT data. Optionally, the method further comprises automatically registering the segmented at least one spinal bone portion to identify at least one spinal vertebrae.

Optionally, the osteoporotic fracture predictive factor includes a confidence grade of the risk factor.

Optionally, the CT scan is ordered for a conventional clinical indication including at least one member of a group consisting of: low dose CT scan of the chest to screen for lung cancer, CT scan to screen for colon cancer, standard non-contrast CT scan of the chest, IV contrast CT scan of the chest, standard non-contrast CT scan of the abdomen, IV contrast CT scan of the abdomen, oral contrast CT scan of the abdomen, pelvic CT scan.

Optionally, the method further comprises detection of osteoporosis fractures and an indication for the position of the detected fracture.

Optionally, the method further comprises applying the classifier to certain extracted features to generate a feature time change function defining a change in value of the certain extracted features over time.

Optionally, the risk is calculated with statistical certainty when less than all of the available extractable features are successfully extracted as determined based on a validity score.

Optionally, the method further comprises selecting the classifier from a group of available classifiers based on a time interval between the current scan of the patient and a previous scan of the patient.

According to an aspect of some embodiments of the present invention there is provided a computer-implemented method of training an osteoporotic fracture classifier for use in a process to predict risk of osteoporotic fracture, comprising: receiving a corpus of training image files, the training image files comprising data of a CT scan of a body image of at least one patient containing at least one bone portion, the CT scan having being performed with settings selected for imaging of non-osteoporosis related pathology, each respective training image being associated with either a patient diagnosed osteoporosis, or a patient without an osteoporosis diagnosis; extracting features based on the imaging data denoting the identified bone portion in each respective CT scan; and training an osteoporotic fracture classifier based on the extracted features, to provide an osteoporotic fracture predictive factor indicative of osteoporotic fracture risk in the patient.

Optionally, the CT scan includes age and gender information for each respective patient.

Optionally, the method further comprises automatically detecting osteoporosis fractures in at least one of the training image files, and automatically replacing the diagnose of the respective patient in the training set based on the detected fracture.

Optionally, not all the features are extracted for all the patients in the training corpus.

Optionally, different methods are used to extract the same feature in different files.

Optionally, the method further comprises normalizing the training image files based on imaging parameters such that extracted features from different CT scans are standardized for comparison to one another.

Optionally, at least some of the training file images are low resolution images being inadequate for calculation of bone mineral density, and training comprises training the osteoporotic fracture classifier to compensate for the low resolution by combining together data from the extracted features to increase the statistical certainty of risk classification above a random guess.

Optionally, the corpus of training images include images of the same patient obtained at different periods in time that are long enough to detect statistically significant changes in at least some of the extracted features, wherein the osteoporotic fracture classifier is trained to predict the risk of developing at least one osteoporotic fracture at a certain future time frame based on the statistically significant changes in the extracted features.

Optionally, the corpus of training images includes images of the same patient obtained at different periods in time that are long enough to detect statistically significant changes in at least some of the extracted features, wherein the osteoporotic fracture classifier is trained to predict the risk of having at least one osteoporotic fracture at a certain future time frame based on the statistically significant changes in the extracted features.

Optionally, the corpus of training images include images of the same patient obtained at different periods in time that are close together, and with no treatment that accelerates the osteoporosis diagnosis change, so that statistically significant changes in one or more extracted features are not expected, and validating the extracted features based on lack of statistically significant changes.

Optionally, the method further comprises assigning a validity score to each of the extracted features denoting estimated success or failure of the respective extracted feature based on the ability of correctly extracting the respective feature from the imaging data, and excluding extracted features having validity scores below a threshold.

Optionally, the corpus of training images includes a least one CT scan of the same patient before developing osteoporosis and at least one CT scan after developing osteoporosis.

Optionally, the corpus of training images includes a least one CT scan of the same patient before developing an osteoporotic fracture and at least one CT scan after developing the osteoporosis fracture.

Optionally, the corpus of training images include at least one CT scan of the patient diagnosed with osteoporosis before initiation of medical therapy to treat the osteoporosis, and at least one CT scan of the same patient after treatment with the medical therapy.

Optionally, the corpus of training images are of patients having common demographic characteristics.

Optionally, the corpus of training images are of patients having common pathology.

Optionally, the method further comprises automatically detecting osteoporotic fractures in at least one of the training images of the corpus of training images, wherein a patient has a set of training images in which a first earlier image does not contain the detected fracture, and a later acquired image in which the fracture has been automatically detected.

Optionally, the method further comprises defining healthy values of each extracted feature and abnormal values of each extracted feature associated with a risk of osteoporotic fracture, each defined value being predictive of the risk of developing osteoporotic fracture. Optionally, the healthy values are defined based on a demographic group. Alternatively or additionally, the healthy values are predefined for existing pathology of the respective patient. Alternatively or additionally, a function is defined to adjust the healthy values for each respective patient according to demographic and/or medical information of the respective patient. Alternatively or additionally, the healthy or abnormal values per patient are part of the system output. Optionally, the output of the system includes a notification denoting the differences between the values of the extracted feature of each respective patient and healthy values. Optionally, the method further comprises applying a predefined function that adjusts the healthy values to specific body part and/or scan characteristics.

Optionally, the method further comprises receiving patient medical history parameters, and wherein training further comprises training the osteoporotic fracture classifier based on the medical history parameters.

Optionally, the method further comprises training multiple classifiers, wherein each classifier is trained to be applied for a different time interval between subsequent imaging scans of a patient.

Optionally, the method further comprises validating the trained classifier based on one or more validation criteria selected from the group consisting of: validating that the risk prediction results obtained with an extracted parameter denoting a new fracture feature obtained from a patient medical record and risk prediction results obtained without the extracted parameter are similar within an error threshold, the risk for fracture does not decrease over time, and the result per patient imaging file provides a risk that monotonically increases in time.

Optionally, the method further comprises creating a virtual scan feature to train the classifier with additional features between two imaging files of the same patient spaced apart in time.

According to an aspect of some embodiments of the present invention there is provided a system for predicting risk of osteoporotic fracture, comprising: a hardware processor; an interface for receiving imaging data of a computed tomography (CT) scan of a body of a patient containing at least a bone portion, the CT scan being performed with settings selected for imaging of non-osteoporosis related pathology; a memory having stored thereon program modules for instruction execution by the processor, comprising: a bone identification module for processing the imaging data to identify the bone portion; a feature extraction module for extracting features based on the imaging data denoting the identified bone portion; a classifier module for computing an osteoporotic fracture predictive factor indicative of the risk of developing or having at least one osteoporotic fracture in the patient based on the extracted features, the osteoporotic fracture predictive factor calculated by applying a trained osteoporotic fracture classifier to the extracted features, the osteoporotic fracture classifier trained from data from multiple CT scans performed with settings selected for imaging non-osteoporosis related pathology; and an output unit for providing a signal indicative of the osteoporotic fracture predictive factor.

Optionally, the signal indicative of the osteoporotic fracture predictive factor is provided when not all the extractable features are extracted.

Optionally, the system further comprises a normalizing module for normalizing the received CT scan such that the extracted features may be classified by the classifier.

Optionally, the system further comprises a training module for training the osteoporotic fracture classifier based on a corpus of training imaging files from at least some patients diagnosed with osteoporosis that have undergone imaging for non-osteoporosis related pathology. Optionally, the system further comprises a resource limited module for training the osteoporotic fracture classifier when system resources are limited. Optionally, the training module resides on a remote server that provides the trained osteoporotic fracture classifier over a network connection, for local analysis by the classifier module. Optionally, the training module trains different osteoporotic fracture classifiers based on different patient populations, and provides the specific patient population osteoporotic fracture classifier for local analysis at a clinic serving the respective specific patient population. Optionally, all software modules reside on a server of a health organization entity for training the classifier based on the stored imaging files and applying the trained classifier to newly acquired imaging files.

Optionally, the software modules are installed on a radiology workstation.

Optionally, the feature extraction module applies a first feature extraction method to the received imaging data, the first feature extraction method being different than a second extraction method used to train the classifier.

Optionally, the feature extraction module selects a certain feature extraction method from multiple feature extraction methods to extract features from each respective received imaging data file, the certain feature extraction method selected based on scan characteristics used to acquire the respective imaging data file.

Optionally, the feature extraction module selects a certain feature extraction method from multiple feature extraction methods to extract features from each respective received imaging data file, the certain feature extraction method selected based on CPU and/or memory constraints.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
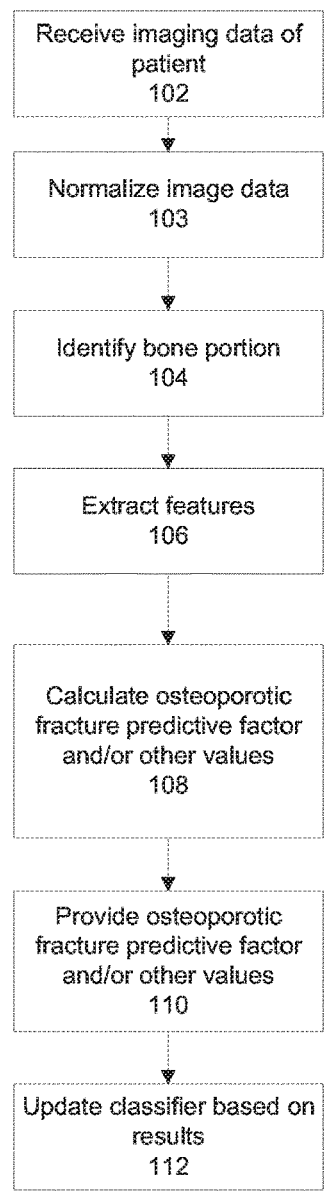
FIG. 1 is a flowchart of an exemplary method of computing an osteoporotic fracture predictive factor based on imaging data, in accordance with some embodiments of the present invention.

As used herein, the term osteoporosis is sometimes meant to include osteopenia, and/or to include different classifications of osteoporosis and/or osteopenia which are currently defined (e.g., primary osteoporosis (e.g., type I, type II), secondary osteoporosis) and/or which may be defined in the future.

As used herein, the term fracture is used to refer to osteoporotic fracture. In osteoporotic fractures, the bone is fractured as a result of normal activities, for example, falling from a standing height or less. The bone would not be expected to break in patients without the underlying medical condition. Common sites of osteoporotic fractures include spine, hip, wrist, humerus and pelvis. Osteoporotic fractures may result in complications, for example, limitation of ambulation, depression, loss of independent and/or chronic pain. Osteoporotic fractures in certain bones, such as the hip, are associated with an increased risk of mortality, while fractures in the spine may be rarely noticed. The systems and/or method described herein may be based on the assumption that bone fragility is the same in the spine and the hip, and that the fracture of risk in either location is similar, for example, within a predefined range. The systems and/or methods described herein predict the risk of osteoporotic fractures, which may be prevented and/or treated early on, to help reduce or prevent complications.

As used herein, the term image refers to any type of medical image (for example, 2D or 3D) and may include the age and/or the gender of the patient. Additional information may be extracted from the EHR as described herein.

As used herein, the term CT is sometimes interchangeable with the broader term imaging modality, as the systems and/or methods described herein may not be necessarily limited to CT, as other imaging modalities may be used as a basis for the methods and/or systems described herein, such as magnetic resonance imaging (MRI), standard X-rays, or other imaging modalities. The methods and/or systems may be applied to other imaging modalities that satisfy the following constraints: presence of existing fracture may be detected, bones may be segmented from the acquired images, and predictive features may be automatically extracted and classified from the imaging data.

As used herein, the terms features and parameters are sometimes interchangeable, as both may refer to inputs into a method (e.g., trained classifier) for calculating the fracture risk as described herein. Generally, the term features relates to, but is not necessarily limited to, inputs extracted from imaging data, and the term parameters relates to, but is not necessarily limited to, inputs extracted from the patient medical history such as the EHR.

An aspect of some embodiments of the present invention relates to systems and/or methods for predicting the risk of a patient developing one or more osteoporotic fractures based on data from an imaging modality (e.g., computed tomography (CT)) scan performed with settings selected for imaging of non-osteoporosis related pathology. The prediction may take place based on retrospective analysis of imaging modality data (for example, on pre-stored data), and/or real-time analysis of imaging modality data (for example, the risk is calculated after acquisition of new imaging modality data from the patient), regardless of the presence or absence of known osteoporotic precondition(s). The systems and/or methods described herein may calculate the risk of fracture in patients that were not identified as being at-risk of fracture. In case of detection of osteoporosis fractures, this information will be added to the known diagnosis or replace the current diagnosis.

Optionally, the prediction includes automatic detection of minor and/or severe osteoporosis fractures, in the set of training images and/or the patient file being analyzed, using automatic or semi-automatic procedures. The detected fractures may have been missed or ignored during previous readings and/or analysis, as the imaging data has not been acquired to diagnose osteoporosis related conditions.

The prediction may be based on a certain bone, a group of bones, and/or in general. For example, the first bone or group of bones to have a bone mineral density defining osteoporosis, and/or the first bone or group of bones to be fractured. The prediction may include a probability of the risk, for example, about 75% chance, about 60-80% chance, or other probability values and/or ranges. The prediction may include a time frame related to the risk, for example, risk of developing fracture in about 3-5 years, or in less than 1 year, or other time frames. The prediction may include a probability related to the time frame and/or risk, for example, about 75-85% risk of developing fracture in about 3-5 years, about 50% risk of developing fracture in less than 1 year, 20% risk of fracture in about 1 year, 50% risk of fracture in about 3 years, and 90% risk of fracture in about 5 years. Exemplary predictive factors of osteoporotic fracture include: at risk, not at risk, low risk, medium risk, high risk, risk of about 50% or about 75% or other values, risk of about 20-50%, risk of about 75-90% or other value ranges, or other predictive factors. The prediction may include the effects of medical conditions and/or medical treatments that may lead to secondary osteoporosis and/or fracture, such as gastrointestinal disease, bone marrow disorders, endocrinopathies, malignancy, drugs (e.g., corticosteroids, chemotherapy), or other medical conditions and/or medical treatments. The medical conditions and/or medical treatments may be obtained, for example, automatically from the patient EHR and/or from the CT referral. The prediction may be based on other factors, such as race, osteoporosis risk factors and/or the like in combination with the imaged data.

As described herein, inventors discovered that imaging modality files acquired for reasons other than evaluation and/or diagnosis of osteoporosis related pathology provide a basis for automatic machine based learning, to predict the risk of osteoporotic fracture in a patient. Such imaging modality files serve as a training set for training a classifier for predicting the fracture risk as described herein. The training images for creating the classifier(s) may be based on a corpus of imaging modality files (e.g., conforming to the Digital Imaging and Communications in Medicine (DICOM) standard). At least some of the files are associated with an osteoporosis related diagnosis, although the imaging file may not be directly related to an osteoporosis related diagnosis, for example, the osteoporosis related diagnosis may be part of the patient medical history. In this manner, use of a general corpus of imaging modality files may provide a very large base of files for the machine learning, which may enable prediction of fracture with a clinically significant accuracy (i.e., to screen patient at risk of osteoporotic fracture), for example, as compared to special medical image files acquired to diagnose osteoporosis.

Optionally, the training images include images of the same patient obtained at different periods in time that are long enough to detect statistically significant changes in one or more extracted features related to risk of fracture, for example, multiple CT scans separated by at least about 1 month, or at least about 3 months, or at least about 6 months, or at least about 1 year, or at least about 3 years, or at least about 5 years, or at least about 10 years, or other smaller, intermediate or larger time periods. Such training images may serve as a basis for training the classifier to predict time associated fracture risk (as described herein) based on the changes. Alternatively or additionally, the training set includes multiple scans of patients with shorter time differences, such as when patients are within factors known to accelerate the osteoporosis process, for example, during chemotherapeutic treatment. Alternatively or additionally, the training images include images of the same patient obtained at different points in time that are close together so that statistically significant changes in one or more extracted features related to risk of fracture are not expected, for example, CT scans separated by no more than about 1 day, or no more than about 1 week, or no more than about 2 weeks, or no more than about 1 month, or no more than about 3 months, or other smaller, intermediate, or larger time periods. Optionally, patients having the images close together in time are not being treated with osteoporosis accelerating medical treatments, for example, chemotherapy. Such training images may be used to validate the extracted features based on the lack of statistically significant changes. The different scans may be acquired using different protocols or the scans may be of different body parts. The system may use this information to normalize the parameters, as described below.

Optionally, imaging data acquired from patients undergoing routine imaging (e.g., CT scans) (i.e., not selected for diagnosis of osteoporosis) may undergo additional automatic screening analysis, such as in a by-the-way analysis routinely performed on every acquired medical imaging data for every patient, to estimate the risk of the patient developing an osteoporotic fracture. The additional screening may be performed without requiring additional significant radiologist reading time. There may be some additional radiologist reading time, for example, to supervise the batch output and/or evaluate particular images. The patient may not require additional specialized imaging designed to screen and/or diagnose osteoporosis and/or fracture, which may expose the patient to additional radiation. The fracture risk stratification does not require dedicated scan settings, and/or additional hardware. The risk prediction may be performed based on existing equipment, such as by installation of software modules to perform the methods described herein. The risk of osteoporotic fracture may be estimated before the patient experiences symptoms related to osteoporosis and/or fracture, and/or before standard osteoporosis tests diagnose osteoporosis and/or osteopenia and/or osteoporotic fractures.

The acquired imaging modality files (used for training or being analyzed for risk) may be unsuitable for automatic diagnosis of osteoporosis by available computerized methods, such as not containing suitable data for calculation of BMD and/or other osteoporosis related measurements that may serve as a basis for diagnosis of osteoporosis. The CT data is not collected as part of a CT scan ordered to measure BMD and/or diagnose osteoporosis, such as a quantitative CT scan, for example, calibration phantoms were not present during the CT scan.

The CT scan may have been ordered for a conventional clinical indication, for example, low dose CT scan of the chest to screen for lung cancer, CT scan to screen for colon cancer, standard non-contrast CT scan of the chest, intravenous (IV) contrast CT scan of the chest, standard non-contrast CT scan of the abdomen, IV contrast CT scan of the abdomen, oral contrast CT scan of the abdomen, pelvic CT scan, or other CT study protocols. The CT scan may have been ordered, for example, to help determine the cause of a bowel obstruction, to help diagnose appendicitis, assess complications of pancreatitis, screening for color cancer (i.e., virtual colonoscopy), evaluation of the urogenital system (i.e., CT urography), pre-operative work-up, or other reasons.

The calculation of the osteoporosis fracture risk by the systems and/or methods described herein is based on multiple parameters, and significant risk of fracture may be calculated even for patients with normal BMD, as abnormal BMD is traditionally used as a basis in the art for prediction of osteoporosis.

In contrast to the systems and/or methods described herein, which use stand acquired image data to predict fracture risk, dedicated equipment exists for measuring BMD for diagnosis of osteoporosis, such as Dual-energy X-ray absorptiometry (DXA). DXA is generally underutilized (many patients that are candidates for screening do not undergo the imaging procedure), and not sensitive and/or specific enough for accurate diagnosis, as diagnosis depends on measurement of BMD, which is only a single parameter. DXA is based on a 2D image, unable to capture variations in bone density occurring anterior and/or posterior to the imaged bone slice. CT provides 3D imaging data, which may provide such volumetric perspectives. Certain methods, such as QCT may be more sensitive and/or specific than DXA, but require an imaging phantom during the image acquisition, special scan parameters, and/or an osteoporosis related indication for the patient to undergo imaging. Although bone mineral density (BMD) is sometimes calculated based on dedicated equipment such as DXA, systems and/or methods may exist for estimation of BMD based on CT-data, for example, as described by Pickhardt et al, "Opportunistic Screening for Osteoporosis Using Abdominal Computed Tomography Scans Obtained for Other Indications", Ann Intern Med. 2013; 158:588-595, incorporated by reference herein in its entirety. The data of the imaging modality (e.g., CT) scan used by the methods and/or systems described herein may be inadequate and/or unsuitable for calculation and/or estimation of a bone mineral density for diagnosis of osteoporosis, for example, as per the method as described by Pickhardt and/or other known methods.

Data collected from imaging modalities other than CT may be used as a basis for predicting fractures based on the systems and/or methods described herein. For example, quantitative ultrasound techniques to evaluate bone microarchitecture may be used to predict fracture risk. Optionally, the preferred site is the calcaneus, because it is readily accessible to handheld ultrasound with minimal artifacts from intervening tissue, but other locations and/or other bones may be used.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3:
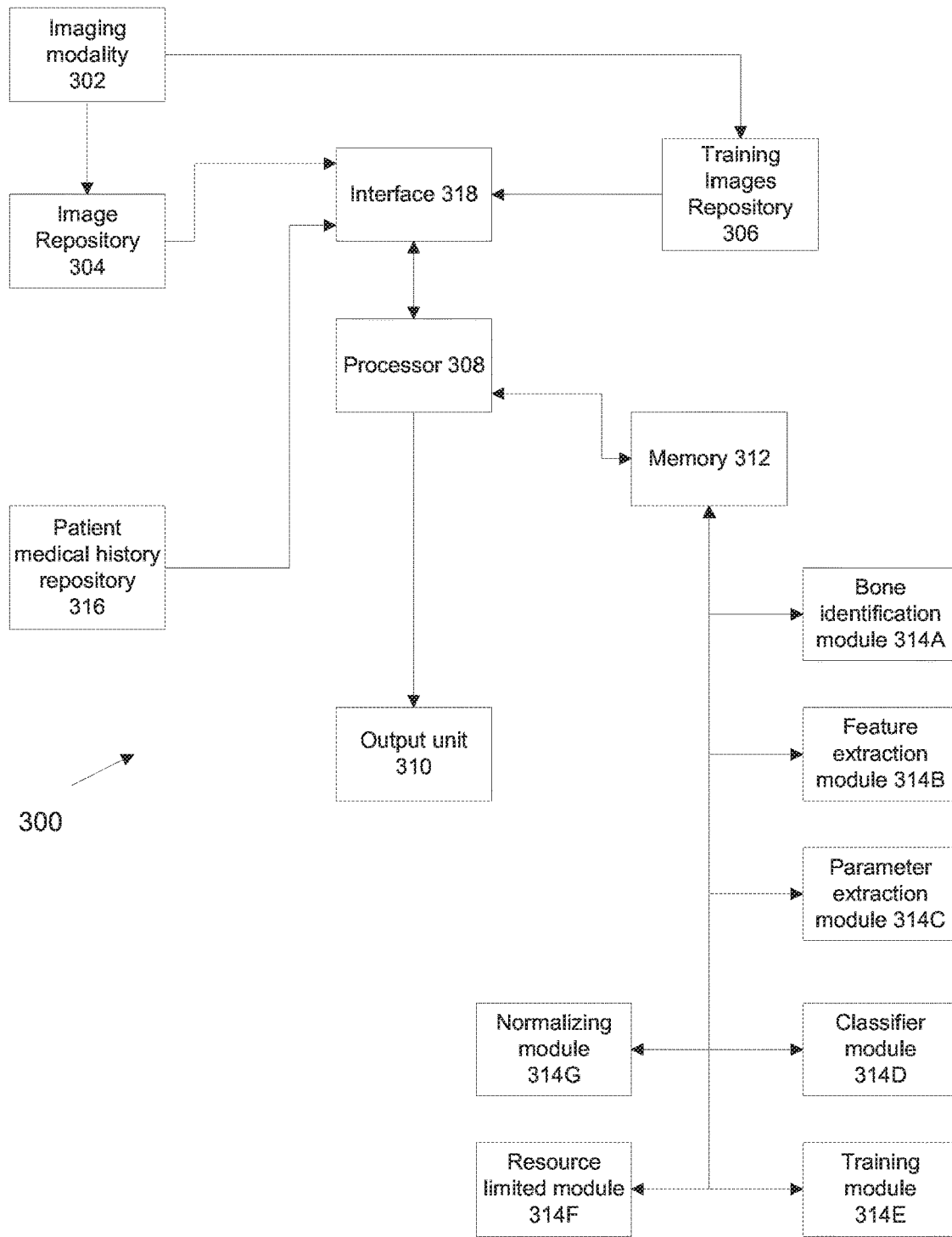
FIG. 3 is a block diagram of an exemplary system for computing an osteoporotic fracture predictive factor and/or for training a classifier(s) for computing the osteoporotic fracture predictive factor, in accordance with some embodiments of the present invention.

Reference is now made to FIG. 1, which is a flowchart of an exemplary method of calculating an osteoporotic fracture predictive factor based on CT image data (or data from other imaging modalities), in accordance with some embodiments of the present invention. The CT image data is obtained during a routine scan for non-osteoporosis related pathology. Reference is also made to FIG. 3, which is a block diagram of an exemplary system 300 for calculating an osteoporotic fracture predictive factor and/or for training a classifier for calculating the osteoporotic fracture predictive factor, in accordance with some embodiments of the present invention. System 300 may execute the method of FIG. 1.

System 300 may include one or more processors 308 in electrical communication with one or more memories 312, which may store one or more modules having instructions for execution by processor 308, as described herein. Processor 308 may be in electrical communication with one or more interface(s) 318 for receiving CT image data (e.g., from an image repository 304 and/or training images repository 306) and/or other data such as patient medical history or the EHR. Different interfaces 318 may be provided, for example, a first interface to receive the imaging modality data and a second interface to receive the patient medical history.

System 300 may include an output unit 310 for providing signals denoting the calculated osteoporotic fracture predictive factor and/or other calculated value. The osteoporotic fracture predictive factor may be displayed on a monitor, stored on a memory for future access, and/or forwarded for further processing.

System 300 may be implemented in various embodiments, for example, software modules loaded onto an existing radiology workstation for processing medical image data after acquisition, a hardware module for plugging into the existing radiology workstation, a remote computer running software that receives the medical image data through a network connection, or other architectures.

System 300 may be divided into two separate systems, such as a first system for training the classifier, and a second system for applying the classifier to acquired medical image data. The first system may reside at a central location, such as on a central server, providing the trained classifier to multiple remote locations having the second system, such as radiology workstations. Each radiology workstation receives the trained classifier, and locally applies the classifier to the acquired image data to predict fracture risk in the patient having been scanned. Other system architectures may also be used. For example, the classifier training and application of the classifier occur within the same server, such as a server of a health management organization (or other healthcare entity) that houses imaging records for clients. The classifier may be trained on the stored data set, and applied to each new imaging record being added to the data set (i.e., newly acquired images).

Optionally, the radiology workstation receives one or more separate classifiers for different populations, such as distinct patient populations being served by the respective client. For example, a woman's health clinic may receive a classifier designed for females (i.e., trained on data from women only), a gastrointestinal clinic may receive a classifier designed for patients with intestinal absorption problems (i.e., trained on patients with malabsorption related conditions), and an autoimmune disease clinic may receive a classifier designed for patients taking steroids (i.e., trained on patients treated with steroid). In another option, the physician/user may add additional medical information to enable more accurate results.

Optionally, at 102, CT image data (or imaging data from another imaging modality) of the patient is received, for example, from an image repository 304, which may store CT image data obtained by a CT scanner 302.

The CT scan may have been acquired with or without contrast agent. The CT scan may have been acquired at various dose levels. The CT scan may have been acquired with different settings.

Optionally, at 103, the CT scan data is normalized to allow fracture risk calculation based on a training set of imaging data, for example, by a normalizing module 314G. The received imaging file may be normalized to allow comparison between extracted features. Alternatively or additionally, one or more normalization factors are calculated for the extracted features such that the extracted features are comparable between different CT scans of predefined set of protocol and body parts. As the received imaging data may vary (for example, different scanned body areas, different scanning protocols, different radiation levels) not all extractable features may be valid for each received imaging file. The influence of each extractable feature may be quantified.

Optionally, the received CT scan is normalized based on radiation dose such that the extracted features are comparable between different CT scans for standardized classification by the osteoporotic fracture classifier. Alternatively or additionally, the CT scan is normalized based on one or more imaging parameters, for example, KPV, mA, contrast enhancement, and other relevant parameters.

Alternatively or additionally, the medical data of the patient, such as the EHR data is standardized to allow comparison with one another, for example, definitions are standardized, and/or measurement units are standardized. Different patients may have different information available in their EHR.

Optionally, normalization is performed as part of the extraction of features and/or parameters based on an assigned validity score denoting estimated success or failure of the respective feature and/or parameter. The validity score may be calculated based on the ability of correctly extracting the respective feature and/or parameter from the imaging data. Not all features and/or parameters may be extracted for every type of image, as images may vary, for example, by quality, by radiation dose, and by body part being images. In such cases, the risk may still be calculated when less than all of the extractable features are (or may be) successfully extracted. The score may be automatically calculated, for example, module 314G and/or by feature extraction module 314B and/or parameter extraction module 314C as part of the extraction process described herein. Certain scores (for example, below a threshold) may denote a failure in correct extraction. The associated feature and/or parameter may be excluded. The scoring method may prevent or reduce the use of incorrect features during the risk calculation. Certain scores may denote that the feature requires additional validation by other processing methods. The score value may affect the weight assigned to the extracted features as part of the risk calculation process, and/or may affect the confidence level of the determined risk.

Alternatively or additionally, other methods of normalization may be used. For example, images may be processed to normalize the pixel intensity values (for example, based on the radiation dose) to a common reference, images may be registered to a common coordinate system, images may be classified into different categories to reduce intercategory variations, or other suitable methods.

Optionally, at 104, a bone portion is automatically identified, for example, as described with reference to FIG. 4, for example, by a bone identification module 314A.

Optionally, bone portions of the spine are identified. Alternatively or additionally, bone portions of other parts of the body may be identified. The spine may be selected, as the spine tends to appear often in many CT scans of the body, such as a chest scan, an abdominal scan, a pelvic scan, and/or a full body scan.

As used herein, the term spine or axial skeleton may sometimes be replaced with the broader term body bone, as the systems and/or methods described herein are not necessarily limited to the spine, but may be used for other bones of the body.

Optionally, at 106, features are automatically extracted. Features may be extracted based on the method described with reference to FIG. 5. Features may be extracted from the imaging modality data. Parameters related to the patient medical history may be extracted from the patient EHR, from the imaging modality data, and/or using other methods.

Different feature extraction methods may be applied to extract features from the received imaging data, and to extract features from the corpus of training image files used to train the classifier. Optionally, a certain feature extraction method is selected (e.g., automatically by the feature extraction module) from multiple available feature extraction methods, to extract features from each respective received imaging data file. The certain feature extraction method may be selected based on scan characteristics used to acquire the respective imaging data file, for example, resolution, body part being scanned, contrast status (with or without), resolution, or other parameters. Different sub-sets of features may be selected for processing by the different respective methods. Different functions or analysis method may be applied to calculate the risk from the features.

The predictive features and/or parameters may be provided with respective confidence grades. The confidence grades may be used in the calculation of block 108. The confidence grade represents the perceived evaluation error. The confidence grade may be lower, for example, when only some of the extractable features and/or parameters are available for the patient, and/or when the image quality is low.

It is noted that each predictive feature on its own may be weakly correlated with a risk of fracture, such as having a correlation level similar to a random guess, or only slightly above a random guess. Each respective predictive feature may be unsuitable on its own for predicting the fracture risk. The predictive features may be combined together to obtain a predictive factor with high correlation (significantly above a random guess) to development of fracture, for example, by boosting together multiple weak classifiers as described with reference to block 108.

The boosting method may be an adaptive boosting method. For example: The most significant feature(s) that apply correct classification on the largest group of the un-classified imaging data may be identified. The weak classifier may be applied to the group of imaging data. The weight of the feature as a function of the size of the classified imaging data may be calculated. The method may be iterated until a prespecified portion of imaging data is classified. The output of the method may be a weak classifier of the imaging data features and the calculated weights. The weak classifier may be applied on new imaging data to classify the imaging data. The overall output of the method may denote the significance of each feature based on the assigned weight. The method may be modularized, and may use only the first N parameters. Selecting N may control the accuracy and/or confidence of the method.

At 108, one or more osteoporotic fracture predictive factors are calculated. Optionally, the osteoporotic fracture predictive factor is calculated by applying a trained osteoporotic fracture classifier to the extracted features, for example, by classifier module 314D of FIG. 3. Alternatively, other methods may be used to calculate the osteoporotic fracture predictive factor, such as using a hash-table, using a mapping function, using predefined equations, and/or other methods.

Optionally, the risk assessment is based on one or more of the weak classifiers, where each weak classifier is unable to calculate the predicted fracture risk based on the extracted feature(s) with a statistical certainty above a random guess, or slightly above a random guess, for example, no more than about 1%, or about 5%, or about 10% or other values. Optionally, the osteoporotic fracture classifier is based on one or more weak classifiers, such as based on a boosting method (for example, adaptive boosting) to increase the correlation between the extracted features and fracture risk, so that the osteoporotic fracture classifier calculates the predicted fracture risk with statistical certainty above a random guess, for example, at least 10% above, or at least 25% above, or at least 40% above, or other values.

Optionally, the method predicts an event of one or more osteoporosis fractures, as the probability that a new fracture will occur in the patient. Existing fractures may affect probability of subsequent fractures. Optionally, the new fracture is predicted within a predicted or predefined time period. Alternatively or additionally, the method provides a rating for the bone states of the patient, for example, from healthy bones with strong trabecular and/or cortical regions to bones with severe osteoporotic fractures.

Optionally, the classifier is selected from a group of available classifiers based on the time interval between the current scan and a previous scan, as described herein. For patients with pre-existing scans, the additional scan may be analyzed using the relevant time period classifier. Classification within the time interval between scans may provide improved accuracy in risk prediction.

The risk confidence value may be a function of the number of features and/or parameters used and optionally related confidence grades. The most significant predictive features (i.e., the highest correlated features and/or group of features) may be provided, which may help guide the healthcare worker in obtaining an overall clinical picture.

Optionally, the current bone state grade of the patient may be calculated, for example, by the classifier as described herein. Alternatively or additionally, the calculated risk provides an estimate of the probability of the patient being in a certain bone grade state within a predefined time period. The bone state is dynamic, and may gradually change in time from healthy bones with strong tracebular and cortical regions to bones with severe fractures. The bone state may be graded within a predefined group, and/or based on a continuous scale, for example, 0 for healthy bones (for example, young person before bone depletion), 90 for minor fractures and 100 for severe fractures. The risk may be provided as the probability of being in grade 100 within the predefined time period. When the scan of the patient includes pre-existing severe fractures, the risk is 100%. The risk calculation gives an indication of the bone generation of the patient, including the current stage and/or the risk of severe fractures within the predefined time period. A high risk of severe fractures may indicate that the patient has fragile bones, and may be sent for further follow up by a physician. Patients with known fractures may already be under surveillance.

Optionally, classifier is first applied to the extracted features to calculate the bone grade (as described herein). The risk may be calculated based on the calculated bone grade, for example, by a classifier, a function, or other methods. The calculated bone grade may provide additional details of the patient state, for example, the current patient state, previous patient state and/or cause of the risk.

Optionally, at 110, the osteoporotic fracture predictive factors are provided, for example, through output unit 310.

Optionally, the risk of fracture is provided, for example, as a probability value, with 0 for patients undiagnosed with osteoporosis with no risk factors, to 100 for patients with existing fracture.

The calculated bone grade of the patient may be provided, for example, as a grade within a range of 0 for patient with healthy bones to 100 for patients with existing fractures.

The presence of an existing fracture may be automatically detected in the received patient imaging data. The fracture may be automatically detected by the classifier, and/or by other imaging methods. When fracture has been detected, the location of the fracture and/or severity of the fracture may be provided, for example, written within a report and/or tagged within the analyzed image.

The list of features and/or parameters used in the classification may be provided. The values may be compared to the expected results in patients undiagnosed with osteoporosis. Theses values may be normalized to gender, age and/or other demographic and/or clinical information.

In addition to the probability of fracture risk, the systems and/or methods may provide a set of parameters that give an indication of the current state of the patient as compared to a previous state. These parameters may be used for follow-up to understand the changes from previous scans. The parameters may help track the risk profile of the patient developing fractures, such as an increase in the risk and/or a decrease in the risk. Changes in risk may be based on, for example, initiation of medical treatment and/or initiation of drugs that may cause osteoporosis. The changes may be compared and/or normalized according to the expected change due to the time differences and/or age and/or other medical related changes (for example, other pathologies, or life style issues). In case of change which is significantly different than the expected, the system may give indication in the output. In this manner, the effectiveness of treatments to prevent and/or halt the disease progression may be monitored. The effects of medical conditions and/or drugs in accelerating and/or causing osteoporosis may be monitored.

Optionally, the osteoporotic fracture risk includes an adjusted risk of developing the osteoporotic fracture based on demographic parameters, for example, gender, age and/or ethnicity.

Optionally, at 112, the osteoporotic fracture classifier is updated based on the results of the analysis of the CT scan. The outcome of the current analysis of the patient medical imaging data, along with the imaging data itself may be provided to update the classifier. The patient medical history (e.g., EHR) may be provided to update the classifier. In this manner, the classifier may be dynamically and/or continuously updated with new data, which may improve the accuracy of detecting the risk of fracture.

Optionally, additional medical information is requested to be provided, for example, blood test results. The classifier may be reapplied to the additional information, which may improve the accuracy of the risk calculation and/or confidence grade.

Figure 2:
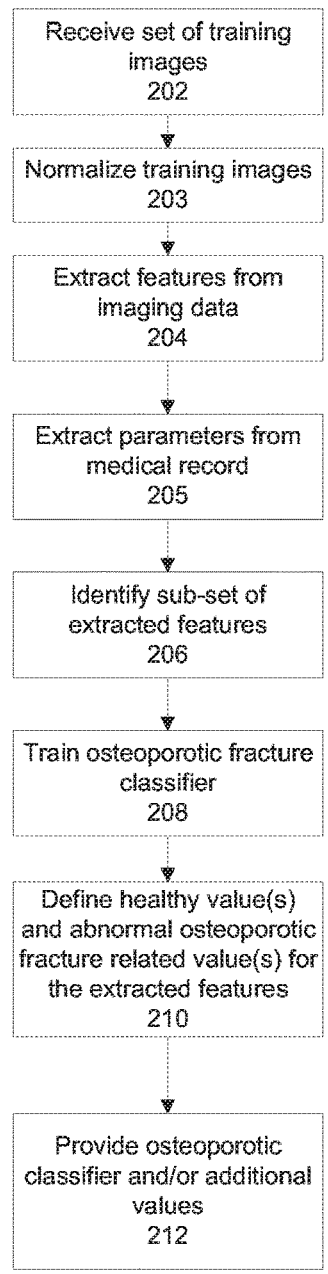
FIG. 2 is a flowchart of an exemplary method of training a classifier(s) to calculate an osteoporotic fracture predictive factor, in accordance with some embodiments of the present invention.

Reference is now made to FIG. 2, which is a flowchart of an exemplary method of training a classifier to calculate an osteoporotic fracture predictive factor denoting risk of fracture, in accordance with some embodiments of the present invention. Optionally, a confidence grade is calculated for the risk. The classifier is trained based on data from CT scans performed with settings selected for imaging of non-osteoporosis related pathology. The learning process may be based on methods of automatic machine learning. The method of FIG. 2 may be executed, for example, by training module 314E of FIG. 3.

Optionally, the set of features and/or parameters and optional associated weights used in the calculation of the predictive factors may be based on a machine learning process of prior diagnosed cases of patients undiagnosed with osteoporosis and/or patients with osteoporosis. The training set may be large, such as in the hundreds of thousands of CT scans, or millions of CT scans. The training set may be classified as big-data. Big-data analysis methods may be employed.

The systems and/or methods described herein may estimate the fracture risk and/or stratify the risk when not all of the patients have all of the parameters. Not all features may be extractable from every imaging data file. Such mismatches in parameters may be compensated for by the large dataset of imaging files. The use of many extractable features and/or parameters may increase the confidence level of the calculated risk, such as by providing adjustments for each patient and/or overcoming variations in CT scanners and/or CT scanning methods.

Optionally, at 202, a set of training images is received, for example, from a training images repository 306, which may be populated with CT imaging data obtained from a CT scanner 302 as described herein. The training CT images are based on data from CT scans performed with settings selected for imaging of non-osteoporosis related pathology.

Optionally, age and/or gender of the patient are included with each respective training image. Risk classification may be statistically different for different ages and/or genders, so that different ages and/or genders are analyzed differently.

The training images may include low resolution CT scans, for example, low resolution CT scans for lung cancer screening. The low resolution is inadequate for diagnosing osteoporosis and/or predicting fracture in the patient based only on the acquired low resolution image. The low resolution image may be inadequate for calculation of bone mineral density. The systems and/or methods described herein compensate for the low resolution of the images, by combining together data from a large number of images. In this manner, although each individual image and/or individual extracted feature may be inadequate for classification for prediction of fracture, the low resolution is compensate for based on an increase in statistically certainty of prediction above a random guess, which is increased by the large number of data samples and/or the large number of extracted features. As described herein, the large number of features and/or data samples is statistically combined to achieve a statistically significant risk prediction. Moreover, additional information, such as from the patient medical record (as described herein), may also compensate for the low resolution, by further increasing the statistical certainty of the risk prediction above a random guess.

The training images may include patients with more than one scan performed at different periods of time. The different scans may be of the same or overlapping body part. The different scans may be of the same protocol or different scanning protocols. The training set may include scans of patients undiagnosed with osteoporosis and/or scans of patients diagnosed with osteoporosis. The scans of patients diagnosed with osteoporosis (e.g., as denoted in the patient medical history, such as in the EHR) are for indications other than osteoporosis. The training set may include scans of the same patient obtained over time, such as before the onset of osteoporosis and/or fracture in the patient and after the onset of osteoporosis and/or fracture in the patient. The patients may be at different stages of osteoporosis, for example, different time periods since onset, different BMD values, and/or different fracture severities. The training set may include patients without any known osteoporosis related risk factors (e.g., medications, medical conditions, family history, lifestyle, and others) and/or patients with known risk factors.

The training set may include images in which fractures have been detected, optionally automatically by the methods described herein. Optionally, at least some patients have CT images in which a first earlier CT image does not contain the fracture, and a later acquired image in which the fracture has been detected. Such sets of data may help train the classifier to automatically predict fractures. Optionally, at least some patients have CT images in which both earlier and later acquired CT images contain fractures. The fracture may have changed, for example, partially healed and/or increased in severity. Such sets of data may help train the classifier to predict progression of fractures and/or stability of fractures.

Optionally, the training set is divided into a group in which no new fractures have been detected between the first and second (or other) images, and another group in which one or more new fractures have been detected between the first and second images. Each group may be divided into sub-groups based on the time period between the two scans. For example, 1 year, 2 years, or other time periods. Other time periods may be adjusted by a weighted division, for example, when the time period is 1.5 years, the event may be mapped by 50% to the 1 year group and 50% to the 2 year group.

Optionally, the diagnosis of the patient having the identified fracture is flagged and/or automatically changed to reflect the detected fracture.

Optionally, the training set includes patients having preselected demographic characteristics, for example, gender, age, and/or ethnicity. Alternatively or additionally, the training set includes patients having a common pathology. Alternatively or additionally, the training set includes patients being treated with similar medical treatments, for example, chemotherapy, or other osteoporosis accelerating meds.

Individual files within the corpus of medical imaging files may be tagged for the presence of existing osteoporotic fracture. Methods of detecting fracture in each respective imaging file include, for example, one or a combination of: a software module that automatically or semi-automatically detects fractures, a manual visual diagnosis of the image by a radiologist, and a method based on information in the patient's EHR.

Individual files within the corpus of medical imaging files used for the training set may be automatically labeled based on information within the medical image file itself, and/or based on related sources, such as the patient EHR. Individual files used for training the classified may be classified based on, for example, an existing diagnosis of osteoporosis, an existing diagnosed osteoporotic fracture, an existing diagnosis of osteopenia, lack of osteoporosis diagnosis, healthy, or other classifications. Alternatively the files are labeled based on a scale, for example, 0 to 100, where 0 denotes a patient undiagnosed with osteoporosis and/or osteoporosis risk factors and 100 denotes a patient with multiple severe osteoporotic fractures, with diagnoses of osteopenia, osteoporosis and individual fractures of various grades having respective intermediate values within the scale. The patient status based on diagnoses and/or medical conditions may be converted to the scale labeling. The scale labeling may provide a simple method to compare patients to each other, but it is noted that non-accurate diagnoses may distort the scale. Alternatively, the files are not labeled, in which case clusterization or other label-less methods may be used as part of the training. Clusters may be generated automatically, for example, using a non-supervised and/or a semi-supervised clustering software module.

The training set of CT images may be initially divided into different categories, where each category is used to independently and separately train different classifiers. The categorization may be performed based on known differences in patient fracture risk, for example, male and female, and/or based on age.

The training set of CT images may be divided into different groups, of patients having only one CT scan, and patients having two or more scans. The group of patients with two or more scans may be further divided, for example, patients with only two scans, and patients with three or more scans, or other suitable divisions. Patients with two or more scans are selected based on significant time differences between scans, where changes in the bones are expected to be detected. The group of patients with multiple CT scans may enable learning about the osteoporosis and/or fracture process, by mapping feature changes between respective scans, for example, allowing time-based risk classification, such as prediction of a time frame for the onset of a fracture, risk of fracture within a certain time frame (for example, within one year), risk of reaching time mile-stones within the process, or other time based predictions. The data of patients having two or more scans within a short time period (which assumes that no change in the patient state occurred between the two scans) is analyzed to evaluate that the output features are similar, since the patient state was not changed. The changes in the features values are expected to be in statistically error or statistical deviation range. The length of the short time period may depend on patient global diagnosis and/or treatment. For example, up to half a year for a healthy patient, but when the patient is under chemotherapeutic treatment, the time period is reduced since the bone depletion process is accelerated by the treatment. Similarly, the long time period may depend on diagnosis and/or treatment, for example, varying by age of the patient.

Patients with CT scans separated by several weeks, months or years may enable learning to predict process velocity, for example, increased risk of early fracture. Patients with CT scans separated by days or weeks may enable learning about measurement stability. As the osteoporosis process has not been expected to proceed quickly enough within the time frame for differences to be detected, changes are not expected. Any variations in measurements may indicate that the measured feature is not accurate, is an error, and/or has large variance in measurement. Such features may be removed, corrected, or corrected for.

Patients with several scans who are under medical treatment may provide information regarding the effect of the treatment on the osteoporosis risk. The treatment may be related to osteoporosis and the comparison may provide information regarding effectiveness of the treatment. Alternatively or additionally, the treatment may be related to another pathology (like chemotherapeutic for cancer) and the comparison may enable measuring the influence of the treatment and/or the pathology on the osteoporosis process.

Sub-sets of imaging files may be selected for training the classifier. For example, training imaging files may be selected based on the patient having three or more scans. In another example, imaging files are selected in patients having three or more scans and a new fracture detected in the latest scan. The sub-set of imaging files may be used to identify the acceleration in risk, as the time when the fracture occurred may be estimated based on the imaging file sequence.

Optionally, the training images are divided into groups for training the classifier to calculate the bone state grade for the patient. The divided training images may be used to train the classifier to predict the risk of a bone grade (for example, 100 denoting severe fractures) within a predefined time period. Imaging files of patients having two or more scans with long time periods between scans may be selected. The selected imaging files may be further sub-divided based on the first and second scan according to exemplary classes:

Class 1: patients with healthy bones (grading not necessarily accurate, having a value <60);

Class 2: patients with minor fractures (grade about 90); and

Class 3: patients with severe fractures (grade about 100).

Patients may be classified based on the change from one class to another between successive CT scans. For example, class 2-3 represents the class of patients that had a change in bone grade significant enough to move their status from class 2 (in the first CT scan) to class 3 (in the next CT scan). Based on the above classification, there may be 5 classes, which may be divided into 2 groups:

Group A: class 1-1; class 1-2; class 1-3; and
Group B: class 2-2; class 2-3.

Patients with severe fractures detected in the first scan may be excluded from the groups. Each group may be further divided into sub-groups based on the time period between the two scans, for example, 1 year, 2 year, or other time periods. Time periods falling in between classifications may be weighted, for example, a 1.5 year may be 50% mapped to year 1 and 50% to year 2.

When fracture information is available, for example, a diagnosis in the EHR, the method may not calculate a risk assessment based on the fracture, as it is assumed that the patient has already been diagnosed.

Any suitable automatic fracture detection algorithm for detecting fractures based on image data may be used for fracture detection.

Optionally, at 203, the received imaging files are normalized to allow comparison with one another, for example, as described with reference to block 103 of FIG. 1.

Alternatively or additionally, the features may be defined as indifferent to the scanning protocol or to the body area, in which case no normalization is needed.

Alternatively or additionally, part of the features (extracted from the images or from the EHR) may be used as optional parameters in the classifiers, and the absence of the parameters may affect the results confidence.

Optionally, at 204, predictive features are extracted from the CT images. Features may be extracted as described with reference to FIG. 5. Optionally, not all features are exacted from each file. Different sub-sets of features may be extracted from different files. Different image processing methods may be used to extract the same feature from different files.

Features may be automatically extracted from the CT images. Features that may not be automatically extracted may be used for tagging the training set.

Extracted features may include the detected fractures in each respective imaging file, as obtained from the EHR and/or automatically determined. The classifier may be validated to ensure that the prediction results obtained with the extracted new fracture feature are similar (i.e., within an error threshold) to results obtained without having the fracture status available, to ensure that the classifier accurately classifies the image when such results are not available, for example, when the fracture status is not in the EHR, and/or the body part in the image does not contain the fracture.

Optionally, at 205 additional parameters are extracted from the patient medical history, optionally taken from the EHR, for example, demographic, medical parameters and/or medical history.

Optionally, at 206, a sub-set of the features and/or parameters is identified. The sub-set may be identified based on relevance and/or importance in the classification process, such as members of the sub-set providing the classifier with high correlation ability. Feature members that do not contribute to improving the correlation effectiveness of the classifier may be removed, without affecting the effectiveness of the classifier. Optionally, the learning process identifies a sub-set of the features and/or parameters, which may be the result of a learning method, such as human, machine learning process or combination of the two.

One or several methods may be found to combine the features and/or parameters to calculate the risk factor and/or confidence grade.

The sub-set of features may be identified before the osteoporotic fracture classifier is generated (i.e., block 208), after the classifier is generated, and/or as part of an iterative process to identify the best sub-set of features that provide the highest correlation effectiveness.

The features may be weighted according to significance and/or importance in calculation of the risk. Some features may be excluded, for example, having negligible influence. Other features may be critical, for example, having significant importance.

Alternatively or additionally, the sub-set is not necessarily identified, but the sub-set is provided. For example, not all features may be available based on the received patient imaging data, some features may be optional, and some features may be excluded due to low quality.

The learning process may be repeated once the sub-set of features has been identified. The repetition may verify that the results are stable.

At 208, an osteoporotic fracture classifier for calculating an osteoporotic fracture predictive factor indicative of the risk of developing fracture is trained. The training may be performed based on one or more suitable methods. Alternatively or additionally, the classifier is trained to calculate the patient bone state grade. Two or more different classifiers may be trained (one or the risk and one for the bone state), for example, in parallel and/or sequentially.

The statistical classifier may be trained based on suitable training methods, for example, a predictive model, data mining techniques, or other methods. Prediction algorithms may be based on machine learning techniques, for example, artificial neural networks, hierarchical clustering, collaborative filtering, content-based filtering, or other methods.

Optionally, the classifier is trained based on supervised learning. Examples of software modules to train the classifier include: Neural Networks, Support Vector Machines, Decision Trees, Hard/Soft Thresholding, Naive Bayes Classifiers, or any other suitable classification system and/or method. Alternatively or additionally, the classifier is trained based on unsupervised learning methods, for example, k-Nearest Neighbors (KNN) clustering, Gaussian Mixture Model (GMM) parameterization, or other suitable unsupervised methods.

Optionally, deep learning methods are applied, for example, using layers of neural networks or other suitable methods. Alternatively or additionally, learning is performed based on a mathematical description of a manifold that separates the data into classes based on the classified training set. Once the manifold has been calculated, CT scans may be classified by finding their location relative to the manifold, with the distance serving as the confidence grade. The mathematical description of the classification process may be back-tracked to individual features and/or parameters to help understand the classification and/or validate the features. In this manner, the sub-set of features that significantly contribute to the classification process may be selected.

Optionally, classification is performed with manual intervention. Trends and/or changes may be analyzed by a human looking at visual representations of data. Manual intervention may assist in tracking processes, identifying significant changes, and trying to understand the effect of single features on the results, and/or the medical interpretation of the change. The manual intervention may be combined with the automated learning methods described herein, for example, the automated method provides input for the manual learning process, and/or the manual process provides input for the automatic process. The automated method may identify the relevant features, and the manual method may help understand the medical significance of the features.

Optionally, classification training is performed in two stages. In a first stage, any pair of scan of a patient having two or more scans separated by time may be independently used to train the classifier. In a second stage, the files may be mapped to a short time frame or a long time frame to train the classifier based on the rate of change of features between the images.

Multiple classifiers may be trained. The multiple classifiers may be combined together and/or applied sequentially and/or in parallel. Optionally, different classifiers are trained for different time intervals between two or more imaging files acquired for the same patient (i.e., the long and short time intervals described herein). Different classifiers may be trained based on the different groups. The classifier may be gradually changed as the time period changes. An exemplary calculation method includes training classifiers based on overlapping time periods, for example, a first group including a 2 year interval of 1 to 3 years, and a second overlapping group including a 3 year interval of 2 to 4 years. Another exemplary method includes overlapping time periods with weights, for example, for a time interval of 2 years and 4 months, 66% is in the year 2 group and 33% in the 3 year group. In this manner, multiple classifiers may be produced, where each classifier is designed for a different time interval between subsequent imaging scans. The different classifiers may be related to one another. For example, the classifier of the 3 year interval is selected to be close to the interpolation based on the classifier of 2 years and the classifier of 4 years.

Optionally, the trained classifier is validated. One or more exemplary validation conditions include: the risk for fracture does not decrease over time, and the result per can per patient provides a risk that monotonically increases in time. When the classifier fails the validation check, the classifier needs to be fixed, for example, re-trained, or flagged for manual intervention and/or investigation for the source of error.

Optionally, the classifier is trained to predict the risk of bone grade as described herein. The classification may be based on the assumption that the risk of developing a severe fracture increases when the bone grade increases (but not necessarily in a linear relationship). Two classifier types may be calculated, a bone grade state classifier and a bone grade risk classifier. Bone grade classifiers may be trained separately on Groups A and B as defined above, or other divisions of the data. The classifier may gradually change as described above, for example, based on overlapping time periods. In this manner, multiple classifiers may be produced, where each grade classifier is designed for a different time interval between subsequent imaging scans.

Alternatively, the bone grade classifier is trained to generate a grade based on a continuous bone grade scale (for example, from 0 to 100) instead of the groups described herein. Such classifier may be used to predict bone grades for patients without fractures.

Optionally, the bone grade classifier is trained based on the imaging files having assigned bone grades. Bone grades may be automatically calculated and/or manually assigned by a radiologist. Imaging files having inconclusive grades may be excluded. Training is based on the extracted features and the assigned bone grades. The generated classifier calculates the bone grade based on the extracted features.

Optionally, the bone grade classifier may be further trained to convert the calculated bone grade into risk of fracture. The bone grade risk classifier may provide additional information of the current state of the patient and/or certain features that vary from healthy values.

A change velocity parameter denoting the rate of change in bone grade for a certain patient may be calculated. For example, when the patient had a grade of 50 two years ago, and now has a grade of 90, the change velocity may be calculated to be 20 grade points per year. Inertia may be calculated in a similar manner.

Optionally, at 210, healthy and/or abnormal values are defined for the extracted features and/or parameters. The healthy values may denote a low risk of developing fracture. The abnormal values may denote a high risk of developing fracture. The healthy values may defined based on demographics, for example, gender and/or age dependent (for example, a healthy woman age 78 may have different parameters than a healthy man age 78 or a healthy woman age 60). The healthy value may depend on other parameters, for example, medical history; healthy values of patient after chemotherapeutic treatment may differ from the values of a patient that was not treated by chemotherapy. The healthy values may be pre-calculated per category or a function may define the adjustment of the global healthy values to the specific patient, for example, adjustments based on the demographics and/or other medical information of the patient. The healthy value may be predefined for existing pathologies.

The healthy and/or abnormal values may be provided as an output together with the risk prediction. Optionally, a difference between the abnormal values of each patient file being analyzed and the normal value is provided as an output, for example, as a summary notification. Abnormal values, the degree of deviation from normal and/or normal values of features may be combined with other clinical data (e.g., physical examination) to gain an overall clinical picture of the patient with respect to osteoporosis.

Optionally, a predefined function is applied that adjusts the healthy values to specific body part and/or scan characteristics. Alternatively or additionally, a predefined function is applied that adjusts the healthy values to age, gender, pathological or demographic condition.

The risk may be defined as function of the difference between the patient vector and the relevant healthy values vector.

Optionally, at 212, the classifier and/or values are provided. Optionally, the classifier is applied in a single interaction, the risk value and optional confidence level is calculated based on extracted features and/or parameters. Alternatively, the classifier is a set of operations that are iteratively applied. Each stage receives a set of features as input and returns a request for additional features to continue the risk calculation process. Each stage may provide a calculated risk with optional confidence grade, which is fine tuned at each iteration until the values stabilize. The iterative method may be more efficient in terms of resource requirements as only features that are relevant at each stage are analyzed.

The method of FIG. 2 may be performed at multiple stages. A first stage may exclude patients with an inconclusive diagnose of osteoporosis. After achieving satisfactory results using patient having confirmed osteoporosis, the results on inconclusive patients may be analyzed and/or validated that the risk probability may be inconclusive, and/or the risks based on the feature and/or parameters set may be further defined.

Alternatively or additionally, the method may be based by learning only from patients undiagnosed with osteoporosis (which may also include no medications and/or medical conditions leading to secondary osteoporosis) and/or patients without an osteoporosis diagnosis, and/or by building the statistics of the features and/or parameters for patients undiagnosed with osteoporosis. At a later stage, the features and/or parameters of osteoporosis diagnosed patients and/or unhealthy (i.e., patients with medical conditions and/or taking drugs that may cause secondary osteoporosis), with or without fracture may be analyzed, which may define the abnormal values that may be related with the risk of developing fracture. A subsequent stage may include an analysis based on the parameters of the inconclusive patients.

Optionally, the classifier generates a feature time change function that defines the change in the values of certain extracted features over time. Additional analysis may be performed on the difference between two groups, such as time interval groups described herein based on the time change function. Such analysis may lead to better understanding of the classifiers.

The method may enable the creation of virtual scan features, the results of which may be validated. When a patient does not have any new fractures detected within the imaging files, virtual scans with interpolated features may be added to help train the classifier. The virtual scans may help train the classifier in circumstances in which the time interval between scans is short or long. For example: scant features are denoted by F1, and scan2 parameters are denoted by F2. When the time difference is 5 years, and a linear features-time-change-function may be used. The virtual scans may be calculated as:

$$F1\_4\ Years = F1*0.8 + F2*0.2 \qquad 1.$$

$$F1\_3\ Years = F1*0.6 + F2*0.4 \qquad 2.$$

$$F1\_2\ Years = F1*0.4 + F2*0.6 \qquad 3.$$

$$F1\_1\ Years = F1*0.2 + F2*0.8 \qquad 4.$$

The generated virtual scans may be added to the training images to train the classifier(s).

Figure 4:
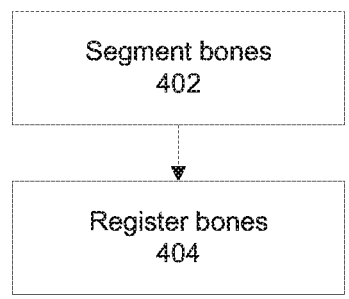
FIG. 4 is a flowchart of an exemplary method of processing imaging data to identify bones, in accordance with some embodiments of the present invention.

Reference is now made to FIG. 4, which is a flowchart of an exemplary method of processing imaging data to identify bones in medical images, such as CT images, in accordance with some embodiments of the present invention. Block 104 of FIG. 1 may be implemented based on the method of FIG. 4. The identified bones based on the method of FIG. 4 may provide a basis for extraction of features, for example, block 106 of FIG. 1, and/or as part of the feature extraction block 204 of FIG. 2.

Optionally, at 402, bones in the CT image are automatically segmented. The bones may be axial bones, such as vertebrae. Optionally, spinal vertebrae are segmented from the CT image data based on suitable segmentation methods.

The segmentation method may be applied before features are extracted.

The segmentation accuracy requirement may not be the same for all features. For example, calculation of the gray level in the vertebra internal section (which may lead to calculation of the BMD or correlated value of the BMD) may not require very accurate segmentation. On the other hand, calculation of the cortical width characteristics may require higher segmentation accuracy.

Vertebra registration may be needed for features that are adjusted to specific vertebra. In some cases, the registration is not accurate and may have error of up to 2 vertebra. For some of the features, the accuracy of the registration has limited effect, especially in features that average information from several vertebrae. In these cases the error in registration may not affect the feature score. In other cases the learning process may be sensitive to the registration accuracy and it may affect the confidence of the results.

The initial segmentation (or the segmentation method) may be based on the Hounsfield value. Segmentation of the bone edges may be calculated using various methods, such as generic bone detection methods and/or specific methods for spinal vertebrae based on structure. Suitable bone and/or vertebrae segmentation method may be used. The segmentation method used may depend on the scanning protocol and/or the body parts and/or the CPU/memory resources.

The segmentation process may be performed as an iterative process where the expected accuracy increase in every stage. The iteration may include stages that apply global segmentation followed by stages that locally correct the segmentation. The local corrections may depend on the bone (vertebra) part or generic processes.

The segmentation process may use more than one segmentation process where the final segmentation may be defined as the highest grade segmentation or by consensus of all methods, or consensus of some of the method according to the grades. The selected segmentation result may be performed globally or locally.

The learning and the patient risk calculation may use different segmentation methods.

Segmentation which is not fully accurate and/or has some inaccuracy in part of the vertebrae edge may produce results that are suitable. The method described herein may be based on multiple extracted features from one or several vertebrae. The methods may be less sensitive to the accuracy of segmentation on specific vertebrae.

Optionally, methods that quantify the segmentation error and/or that identify relevant errors in the segmentation of specific vertebrae may be utilized. In this manner, a poor segmentation process, which may cause inaccurate feature extraction that may lead to significant error in the fracture risk calculation at later stages, may be prevented or reduced.

For each bone segmentation a confidence grade may be calculated.

The grade may be used to calculate the confidence grade of the parameters extracted based on the vertebrae segmentation.

Optionally, at 404, the segmented bones are automatically registered to identify specific bones, such as specific spinal vertebrae.

In various CT scans making up the training set, different parts of the same bone (e.g., spinal vertebrae) may be included in the scan. Some of the extracted featured used in the method described herein may be improved with better registration and/or accuracy.

Registration of the spinal vertebrae may provide additional extracted features, which may improve accuracy of the predicted fracture risk.

The registration may be divided to two main stages. A first registration stage with a defined error, for example, up to two vertebrae. The first stage may be relatively simple to calculate, which may be done using bones segmentation of ribs and/or the basin. The first stage may be significant, as poor accuracy may cause redundancy in the result accuracy. A second accurate registration stage may follow the first stage, to improve the registration accuracy.

The registration process may depend on the body part, the scanning protocol and/or the CPU/memory resources.

The learning and the patient risk calculation may use different registration methods.

The method may provide clinically relevant information regarding the patient even in cases based on part of the features and/or parameters that do not depend on the registration stage.

A registration accuracy confidence grade may be determined, and optionally used to calculate the confidence grade of the extracted features that do depend on registration accuracy.

Figure 5:
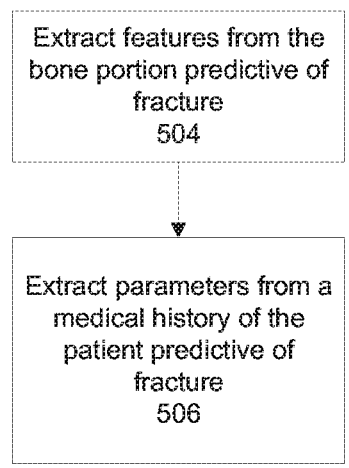
FIG. 5 is a flowchart of an exemplary method of extracting features and/or parameters predictive of osteoporotic fracture, in accordance with some embodiments of the present invention.

Reference is now made to FIG. 5, which is a flowchart of an exemplary method of extracting features and/or parameters associated with prediction of the risk of fracture and/or confidence level of the predicted risk, in accordance with some embodiments of the present invention. The features and/or parameters may be used to calculate the fracture risk and/or confidence level of the risk, as described herein. A sub-set of features and/or related confidence level and/or related weight used in the calculation may be determined, for example, in the learning process described herein. The list of features and/or parameters described is not necessarily limiting, as additional extractable features and/or parameters may be identified and/or added, for example, after additional learning process. The method of FIG. 5 may be used to execute block 106 of FIG. 1, and/or block 204 of FIG. 2.

Features may be extracted based on CT data analysis of one or more bones, for example, one or more specific vertebra or all segmented vertebrae. Features may be extracted based on analysis of the bone (e.g., spinal) structure, the part that was scanned in the CT.

Prediction of the risk of developing fracture may be based on the following two phenomena: a reduction in bone mass and/or a degradation of the micro-architecture of bone tissue. Features may be extracted based on the hypothesis that osteoporosis may due to the following two phenomena: a reduction in bone mass and/or a degradation of the micro-architecture of bone tissue. The extracted features and/or parameters which are described herein are selected to be associated with one or both of these processes, while analyzing information from one or more vertebra.

Optionally, detection of minor osteoporosis fractures may give information regarding the process and/or correlated parameters even in cases where the above two processes were not detected directly.

The extracted features and/or parameters may be based on results of the segmentation of the bones, for example, as described with reference to FIG. 4.

In some of the extracted features and/or parameters, values may depend on the registration (i.e., the value and/or the confidence may depend on the registration confidence).

The extracted features and/or parameters of the bone analysis may be divided to two types. First, internal bone structure characteristics. These features and/or parameters are selected to be associated with the osteoporosis process within the bone and/or may lead to detection before damage is done. Second, bone fracture and/or collapsing features and/or parameters. The features and/or parameters are selected to characterize the bone envelope and/or predict osteoporotic fractures, at early stages and/or before the fracture occurs.

Features may be selected manually and/or automatically. Features may be selected manually, for example, by trained healthcare workers familiar with osteoporosis, based on an educated guess and/or clinical evidence for the feature. Features may be selected automatically, for example, by a software application that clusters related features together. The selection may be performed as a combined process where the automatic selection is the first stage and the trained healthcare worker apply additional selection and/or remove parameters that have no medical rational. The automatic selection may be applied after the manual selection removing parameters that were detected as non effective.

Optionally, at 504, features predictive of osteoporotic fracture are extracted from the identified bone portion of the CT scan, for example, by feature extraction module 314B. The described features may predict fracture in early stages of osteoporosis, or in patients undiagnosed with osteoporosis before loss of bone mass. The analysis may be performed on specific bones (e.g., vertebra), on a group of bones, and/or over all bones in the scan.

The average Housenfield (HU) value of the internal part of the bone (for example, the vertebral medullary portion) may be extracted and/or calculated based on the CT scan data, for example, as described by Pickhardt et al., "Opportunistic screening for osteoporosis using abdominal computed tomography scans obtained for other indications." Ann Intern Med. 2013 Apr. 16; 158(8):588-95, incorporated herein by reference in its entirety. The value may be calculated, for example, in L2, and/or other vertebra. The value may be extracted from one slice of the CT, and/or calculated using volumetric data of the CT and/or by calculating the value from several bones (e.g., vertebrae). An iterative process may be used to iteratively calculate the Housenfield parameter starting from one slice of one vertebra, for example, from the middle of L2 or nearby. It is noted that this calculation may be based on naive and/or low cost segmentation and/or registration algorithms. Later iterations may use volumetric data from one bone (e.g., vertebra) and/or one slice from all segmented bones (e.g., vertebrae). Improved accuracy may be reached by calculating the Hounsfield index based on volumetric information of all the bones (e.g., vertebrae) in the scan. An accurate registration may provide a better tuning of the parameters, when the value calculated relates to specific bones (e.g., vertebra).

The BMD (or correlated value) may be calculated as function of the HU and the scan physical parameters. The function depends on the scans dose, the scans type (with/without contrast agents) and other physical parameters of the scan. This normalization may be done as part of the learning process or by external calculation that the learning may have as input or by combination of the two. Normalization may be performed as described with reference to block 203 of FIG. 3.

The HU based parameter may be calculated in a hierarchy of tuning and/or accuracy. The learning process may lead to the part of the hierarchy that is required to achieve the requested accuracy under performances constrains. Exemplary hierarchy of HU value calculates may be:
- based on one slice, for example, of T12, L1, L2, or other slices;
- based on volume in the internal part of the vertebra, for example, T12, L1, L2, or others;
- based on one slice of each vertebra in the scan, and/or an average of all values;
- based on one slice of each vertebra in the scan, a feature per vertebra;
- based on volume in the internal part of all vertebrae, and/or average of all values;
- based on volume in the internal part of all vertebrae, a feature per vertebra;

statistical description of the above parameters, for example, minimum, maximum, variance, second moment of the HU of the vertebrae;

set of parameters that describes the HU change from vertebra center to the edges, per vertebra;

set of parameters that describes the HU change from vertebra center to the edges, a generic function for all vertebrae in the scan;

symmetry/non-symmetry grading of the HU in the vertebra internal part along the 3 axes; and/or other parameters that may gives parametric description of the vertebrae BMD or correlated value.

The HU value of the internal part may be used as is, and/or relative to HU value in other parts of the vertebra (for example, the cortical part, or the Spinous process) or other organs or detected features (for example, the intervertebral disc or ribs). This calculation be enable better analysis when the CT scan is not calibrated to BMD calculation (such as in QCT).

Parameters may be calculated, and/or features may be extracted related to bone texture, such as texture of the trabecular structure. The degradation of the micro-architecture of bone tissue may be the basis for visual detection of osteoporosis by a human. The texture of healthy patient bone, and osteoporosis patient bones (e.g., vertebra), may be significantly different. Characterizing the bone (e.g., vertebra) internal structure (by one or more parameters and/or features described herein) may provide valuable parameters and/or features for prediction of fracture risk. The texture analysis may initially be performed to characterize a 2D level of one slice of, for example, L2 (or other) bones and/or vertebra (e.g., similar to identification by the human eye) and/or to characterize a 3D level (e.g., similar iterative process as described with reference to the Hounsfield value.) It is noted that the texture calculation may be based on naive and/or low cost segmentation and/or registration algorithms, when looking at the internal part of the bone. The characterization of the texture may be based on various description methods that include representation in the frequency domain or as wavelets. The bone texture feature may have a similar hierarchy as described with reference to the HU above. Additional hierarchy may be created by variances of the number of the features that describes the texture.

Prediction of osteoporosis fracture may be based on predicting a process where bones (e.g., vertebrae) are collapsing and/or at risk of collapsing. An analysis of the bone (e.g., vertebra) boundaries and/or the additional global parameters may predict osteoporosis fracture at early stages, such as before patient signs and/or symptoms and/or before irreversible damage occurs.

Bone dimensions may be calculated and/or extracted, for example, the vertebra size (for example, cortical width) may be calculated and/or extracted. The sizes may be described, for example, by height, width, depth, and/or by the area of the upper plane. These values might be used in the learning process to normalize measurements (for example, in block 203 of FIG. 2). These features may affect the patient fracture risk when normalized with the patient height, weight, BMI or other parameters. The bone dimensions may predict risk of fracture in patients undiagnosed with osteoporosis before bone mass is lost.

One of the indications of osteoporosis may be decay in the cortical section of the vertebra. Thinning of the cortical section may increase the risk of fracture. The vertebral cortical width may be measured on the side edges, as the width may be more clearly visible on the image slices. The cortical width may be preferable for measurements instead of the width of the upper and lower vertebra, as that part of the bone may be adjacent to disk, and may contact another cortex or the next vertebral body, which may lead to incorrect measurements. The vertebral cortical width may have a similar hierarchy as described with reference to the HU above. The measured value may be normalized by bone size and/or compared to normal values as a function of specific vertebra, gender and/or age. Width below normal may lead to a high fracture risk. The width features(s) may be evaluated by one or more of:

based on one slice in T12, L1, L2 or others: average width along the vertebra side edges;

based on volume calculation of T12, L1, L2 or others: average along the height;

based on one slice of each vertebra in the scan: average of all vertebrae;

based on one slice of each vertebra in the scan: per vertebra;

based on volume calculation: average of all values of all vertebrae;

based on volume calculation: per vertebra;

statistical information of the features above, for example, minimum, maximum, variance, second moment of the cortical width of the vertebrae;

set of features that describes the width change along the side edges per vertebra;

set of parameters that describes the width change along the vertebra height per vertebra;

the width of the upper on lower edge of the vertebra(e) per vertebra;

the width of the upper on lower edge of the vertebra(e): average of all vertebra;

symmetry/non-symmetry grading of the edges width in the vertebra plane per vertebra; and/or other features that may gives parametric description of the cortical width.

The vertebra cortical regularity may be calculated and/or extracted. In patients undiagnosed with osteoporosis the vertebra cortex is expected to be regular and/or uninterrupted. A broken cortical regularity may indicate onset of the osteoporosis process. The cortical regularity features may be represented in the frequency domain and/or as wavelets. The cortical regularity may be expressed by statistical information of the cortical part of the vertebra, for example, average HU, minimum, maximum, and variance.

The vertebra upper edge flatness may be calculated and/or extracted. The upper edge flatness parameter may identify a fracture risk, even in early stages. When the upper edge flatness denotes that the upper stage of the vertebra has sunk, the parameter may predict the beginning of an osteoporosis fracture. The flatness parameter may be based on good vertebra segmentation. Improved registration may improve accuracy of fracture prediction. The hierarchy of the flatness feature may be denoted by the number of features used to describe the upper edge plane. For example, described by one feature that indicates the largest distance of the edge from the plane of the edges. An improved description may use multiple features that give indication of the location of the sink. All the values may be normalized to bone size.

The angle between the upper and lower edges of the vertebra may be calculated and/or extracted. In healthy vertebrae the upper and the lower edges are almost parallel. When the fracture process starts, an angle may be formed between the upper and the lower edge, which may be measured. The optimal healthy vertebra angle may be specific. The angle parameter may depend on the bone segmentation, but may be less sensitive to the accuracy than the flatness parameter. The confidence level of the angle parameter may depend on the confidence of the registration algorithm. The angle may be calculated using a 2D axial slice or by calculation of the plane equation of the upper and lower edges of each vertebra. The latter may be more sensitive to fracture since part of the fracture may include tilt.

The spinal structure may be analyzed. The analysis of the spinal structure may provide information about fracture risk. The analysis may be based on the information gathered from the set of vertebrae, such as the relation between its sizes.

The vertebra height may be measured. The height of healthy vertebra may or may not be provided as input to the method. The measurement may be based on the height of the vertebrae in the spinal column that may increase gradually from head to sacrum. Inconsistency in the height change may denote risk of fracture. Height change may be expressed as a function. The height change may have a hierarchy in the number of features used define the height change along the spine. The confidence of the height related parameters extracted from this measurement may depend on the confidence of the segmentation of each vertebra and/or the confidence of the registration.

The similarity of the spinal column of the patient to a healthy model may be compared. The 3D structure of the spine may be compared, for example, the tilt of the spine. The learning process may provide normal spinal column structural features with standard deviation. The learning process may provide information of patients with spinal column structure different than the standard, for example, for patients undiagnosed with osteoporosis with no indicated loss of bone mass, the structure may affect the risk of fracture. In patients with osteoporosis or osteopenia, the structure may indicate onset of the initial fracture process. The hierarchy may be the number of features used to define the similarity. The similarity parameter may be dependent on the registration confidence. The model may be selected to match the age and/or gender of the patient.

Other bones of the body may be analyzed using similar methods to those described above for the spine.

Alternatively or additionally, at 506, parameters predictive of osteoporotic fracture and/or osteoporosis are obtained from the patient medical history, such as from an electronic medical record of the patient and/or from the imaging referral, for example, by parameter extraction module 314C optionally from patient medical history repository 316. The parameters may include, for example, known risk factors, age, ethnicity, gender, smoking status, personal history and/or family history of prior fracture, history of alcohol abuse, history of anorexia, chronic steroid use, height, weight, waist circumference, body mass index and/or family history of hip fracture. Other patient data may be obtained, for example, blood chemistry analyses, such as calcium levels, complete blood count, and tumor markers. Medical conditions and/or drug treatment that may cause secondary osteoporosis may be retrieved, for example, chronic obstructive pulmonary disease (COPD), history of anorexia, history of chemotherapy treatment, chronic steroid use, hyperparathyroidism, and the like. The learning process described herein may identify additional parameters (e.g., from patient records) that may lead to identification of new risk factors correlated with the risk of developing osteoporosis. Medical information that is not currently been correlated with osteoporosis may be included, for example, heart disease history, certain blood test results, other medical test results, and other patient pathologies. Additional parameters identified, for example, based on medical research may be added or removed.

Referring now back to FIG. 3, system 300 may include a resource limited module 314F for executing the methods described herein with limited processing resources. For example, the case of running the method on many historical data sets obtained from CT scans, or even on new CT scans if the processing resources are limited.

Constraints such as CPU resources may influence the method used. For example, lower CPU ability may correlate with degradation in the result confidence. In such a case, tradeoffs between CPU and accuracy may apply as described below. Some of the methods may be iterative: higher CPU resource allocation and/or time provided may increase the resulting accuracy of the specific feature extracted. The iteration may stop at different levels of accuracy. For example, in the risk evaluation process, when significant fractures are detected using a coarse segmentation method, there may not be a need to continue to finer segmentation.

Possible methods of executing the methods with limited resources include a first method of executing a redundant process that may provide lower confidence results. The process may still provide significant improvement by reducing the miss rate for many patients at risk of fracture. A second method is based on an iterative process. In this case, the method is divided to stages. The feature and/or parameter calculation and/or processing order are selected for identification of patients with a low risk threshold for a respective state. Additional calculations may be performed on patients with risk levels above the threshold at every calculation stage. It is noted that the first option may be implemented by using only the first set of the first iteration of the second option.

Figure 6:
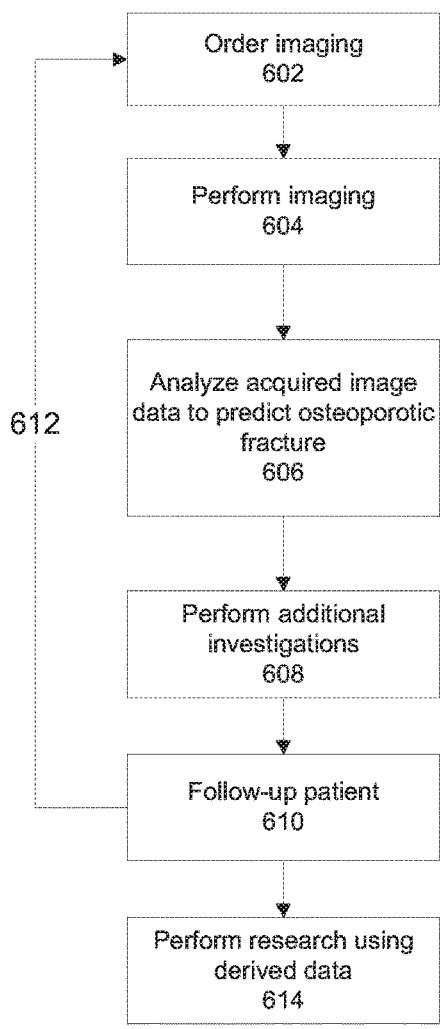
FIG. 6 is a medical method for using a predicted osteoporotic fracture factor based on imaging data, in accordance with some embodiments of the present invention.

Reference is now made to FIG. 6, which is a medical method for using a predicted fracture factor based on imaging data, in accordance with some embodiments of the present invention. FIG. 6 may illustrate the integration of the systems and/or methods described herein (e.g., method of FIG. 1 and/or system of FIG. 3) into medical practice. Prediction of the fracture factor may screen patients for risk of fracture, which may help the healthcare worker decide upon additional investigations. The methods and/or systems described herein may provide a basis for additional research, to learn more about osteoporosis related disease progression.

Optionally, at 602, medical imaging is ordered for a patient, for example, a non-contrast CT of the chest. The medical imaging is ordered to investigate medical conditions other than osteoporosis related pathology, for example, as described herein. The medical imaging may be ordered in patients based on non-osteoporosis related signs and/or symptoms.

Optionally, at 604, the medical image is acquired, for example, the patient is scanned by the CT scanner. The medical image may be acquired with settings that are not suitable to measure BMD and/or perform other investigations to diagnose osteoporosis.

At 606, the acquired medical imaging file is analyzed to predict the risk of osteoporotic fracture, as described herein. The analysis may be performed automatically, as described herein.

The analysis may be performed before the radiology report is prepared, so that the radiology report of the CT scan also contains the predicted risk based on the image.

The analysis may be performed on older acquired images, such as images that have already been analyzed by the radiologist and a report has already been prepared. Such images may be stored, for example, on a storage server at the imaging facility or hospital, on a CD-ROM disc or other portable memory owned by the patient, or at other locations. Optionally, at 608, additional action is taken based on the predicted risk and/or a clinical assessment of the patient.

Optionally, additional investigations are ordered by the healthcare worker of the patient. Alternatively or additionally, the patient is treated to prevent or delay fracture. In this manner, the risk prediction provides a screen of patients at risk of fracture. For example, a patient at high risk of fracture may begin treatment earlier than would otherwise be ordered. Patients unexpectedly at high risk may be identified and investigated further for underlying secondary causes. For example, a patient expected to have a low risk of fracture, but having a high calculated risk may be investigated, for example, to investigate underlying treatable causes, such as malignancy, hormonal problems, gastrointestinal problems, improper drug usage, or other reasons.

The risk of fracture may be used as a control measure to evaluate the impact of other medical treatments that may increase risk of fracture. For example, drugs that are associated with causing osteoporosis (i.e., reducing BMD) may be avoided in patients with high risk of fracture.

The risk may be used by healthcare insurance companies to personalize the cost of insurance coverage to the patient, for example, rewarding patients with low fracture risk with lower insurance cost.

Optionally, at 610, the patient is followed up. The patient may be followed up when imaging data has been subsequently acquired to investigate non-osteoporosis related pathology, such as another CT scan of the chest, or a CT of the abdomen.

The newly calculated risk may be compared to the previously calculated risk. The patient may be followed, to determine if the risk has increased, decreased or remained the same. The patient may be followed to determine the effectiveness of medical treatments that have been started, the effects of osteoporosis causing medical conditions that have been diagnosed, and/or the effects of drugs.

Optionally, a tool is provided to detect changes in bones (e.g., the spinal column) characteristic from previous scan. The probability and/or the vector of parameters may enable detection of changes and/or the disease process. Patients with other problems (e.g., cancer) that may cause damage to the bones, and/or old patients may be followed.

The patient may be treated based on the calculated risk, in some cases, without undergoing additional screening tests such as DXA. Better care may be provided by prevention and/or early intervention and/or treatment when risk of fracture is detected earlier. Cost effectiveness may be achieved by the difference in cost based on early and preventive treatment of fracture over more costly interventions such as surgery to repair the fracture.

The analysis may provide better personal patient assessment and/or diagnosis based on the quantification of fracture risk over time.

Optionally, at 612, the process may be repeated on other acquired images. The patient may be treated, investigated and/or followed by the healthcare team based on the calculated risk results.

Optionally, at 614, research may be performed based on the derived risk prediction data. The systems and/or methods described herein may provide research tools to detect fracture risk factors, osteoporotic fractures, and/or correlated pathologies, while combining the automated detection with additional parameters, such as:

Tools to predict fracture, such as at early stages.
Retrospectively studying existing bodies of clinical knowledge to better understand the impact of various factors on the fracture risk, progress, variations and/or correlated pathologies.
From the parameters set, when patients have had more than one CT scan, the osteoporosis process may be studied, such as disease progression and/or occurrence and/or variations.
Learning more about osteoporosis and correlated pathologies.
Identification of new risk factors correlated with fracture, which may enable improved screening for patients based on other tools than DEXA or CT scan, and/or may facilitate early osteoporosis detection.
Improving the automated fracture detection.

The systems and/or methods may lead to improved identification of the osteoporosis process, relations with other pathologies and/or division of osteoporosis to subdivisions with specific characteristics.

The methods as described above are used in the fabrication of integrated circuit chips.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems and methods will be developed and the scope of the term CT and processor are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer-implemented method for predicting risk of osteoporotic fracture for treatment of a patient, comprising:
   receiving imaging data of a computed tomography (CT) scan of a body of a patient containing at least a bone portion, the CT scan being performed with settings selected for imaging of non-osteoporosis related pathology;
   processing the imaging data to identify the bone portion;
   automatically extracting features based on the imaging data denoting the identified bone portion;
   computing an osteoporotic fracture predictive factor indicative of the risk of developing at least one osteoporotic fracture in the patient, or the risk of the patient having at least one severe osteoporotic fracture, based on the extracted features, the osteoporotic fracture predictive factor calculated by applying a trained osteoporotic fracture classifier to the extracted features, the osteoporotic fracture classifier trained from data from a plurality of CT scans performed with settings selected for imaging non-osteoporosis related pathology; and
   providing the osteoporotic fracture predictive factor for treatment of the patient.

2. The method of claim 1, wherein the bone portion comprises a vertebra, and the osteoporotic fracture comprises a compression fracture of the vertebra.

3. The method of claim 1, further comprising computing a current bone state rating for the patient based on the extracted features.

4. The method of claim 1, further comprising computing an estimate of the probability of the patient being in a certain bone grade state within a predefined time period based on the trained osteoporotic fracture classifier applied to the extracted features.

5. The method of claim 1, wherein the osteoporotic fracture predictive factor includes a time frame for a risk of developing or having at least one osteoporotic fracture.

6. The method of claim 1, wherein the osteoporotic fracture predictive factor is indicative of the risk of developing an osteoporotic vertebral body fracture.

7. The method of claim 1, wherein processing the imaging data to identify the bone portion comprises segmenting the imaging data to extract at least one vertebrae bone, and wherein automatically extracting features comprises automatically extracting features from at least a portion of at least one segmented vertebrae bone.

8. The method of claim 7, wherein the extracted features comprise height of the at least one vertebrae bone along at least a frontal plane, a medial plane, and a back plane.

9. The method of claim 7, wherein the extracted features comprise a loss of height of the at least one vertebrae bone.

10. The method of claim 9, further comprising correlating the loss of height of the at least one vertebra bone with at least one score representing a relation to risk of compression fracture in a population.

11. The method of claim 7, wherein the extracted feature denotes a trabecular texture characteristic of the vertebral trabecular bone structure associated with degradation of the micro-architecture of bone tissue.

12. The method of claim 7, wherein the extracted feature denotes one or both of vertebra cortical width and vertebral cortical regularity.

13. The method of claim 1, wherein automatically extracting features comprises automatically extracting features associated with a risk of osteoporotic fractures.

14. The method of claim 13, wherein the extracted features are associated with the risk of osteoporotic fractures include at least one member of a group consisting of: vertebra upper edge flatness, vertebra upper and lower edge angles, vertebrae height changes, and spinal column similarity to healthy model.

15. The method of claim 13, wherein the automatically extracted features associated with osteoporotic fractures are based on an analysis of the structure of the spine based on identified vertebrae and relation between vertebrae sizes.

16. The method of claim 1, wherein the osteoporotic fracture predictive factor includes a confidence grade of the risk factor.

17. The method of claim 1, wherein the CT scan is ordered for a conventional clinical indication including at least one member of a group consisting of: low dose CT scan of the chest to screen for lung cancer, CT scan to screen for colon cancer, standard non-contrast CT scan of the chest, IV contrast CT scan of the chest, standard non-contrast CT scan of the abdomen, IV contrast CT scan of the abdomen, oral contrast CT scan of the abdomen, pelvic CT scan.

18. The method of claim 1, further comprising detection of osteoporosis fractures and an indication for the position of the detected fracture.

19. A computer-implemented method of training an osteoporotic fracture classifier for use in a process to predict risk of osteoporotic fracture for treatment of a patient, comprising:
receiving a corpus of training image files, the training image files comprising data of a CT scan of a body image of at least one patient containing at least one bone portion, the CT scan having being performed with settings selected for imaging of non-osteoporosis related pathology, each respective training image being associated with either a patient diagnosed osteoporosis, or a patient without an osteoporosis diagnosis;
extracting features based on the imaging data denoting the identified bone portion in each respective CT scan; and
training an osteoporotic fracture classifier based on the extracted features, to provide an osteoporotic fracture predictive factor indicative of osteoporotic fracture risk in the patient for treatment of the patient.

20. A system for predicting risk of osteoporotic fracture for treatment of a patient, comprising:
a hardware processor;
an interface for receiving imaging data of a computed tomography (CT) scan of a body of the patient containing at least a bone portion, the CT scan being performed with settings selected for imaging of non-osteoporosis related pathology;
a memory having stored thereon program modules for instruction execution by the processor, comprising:
a bone identification module for processing the imaging data to identify the bone portion;
a feature extraction module for extracting features based on the imaging data denoting the identified bone portion;
a classifier module for computing an osteoporotic fracture predictive factor indicative of the risk of developing or having at least one osteoporotic fracture in the patient based on the extracted features, the osteoporotic fracture predictive factor calculated by applying a trained osteoporotic fracture classifier to the extracted features, the osteoporotic fracture classifier trained from data from a plurality of CT scans performed with settings selected for imaging non-osteoporosis related pathology; and
an output unit for providing the osteoporotic fracture predictive factor for treatment of the patient.

* * * * *